(12) United States Patent
Tei et al.

(10) Patent No.: US 8,957,173 B2
(45) Date of Patent: Feb. 17, 2015

(54) RESIN PRODUCT FOR MEDICAL USE AND RESPIRATION-ASSISTING TUBE

(75) Inventors: Yuichi Tei, Tokyo (JP); Nobuo Sasaki, Tokyo (JP); Shigeki Suzuki, Tokyo (JP)

(73) Assignees: Next21 K.K., Tokyo (JP); The University of Tokyo, Tokyo (JP); NOF Corporation, Tokyo (JP)

( * ) Notice: Subject to any disclaimer, the term of this patent is extended or adjusted under 35 U.S.C. 154(b) by 600 days.

(21) Appl. No.: 13/265,880

(22) PCT Filed: Apr. 26, 2010

(86) PCT No.: PCT/JP2010/002977
§ 371 (c)(1),
(2), (4) Date: Oct. 24, 2011

(87) PCT Pub. No.: WO2010/122817
PCT Pub. Date: Oct. 28, 2010

(65) Prior Publication Data
US 2012/0097169 A1 Apr. 26, 2012

(30) Foreign Application Priority Data

Apr. 24, 2009 (JP) .................................. 2009-105782
Nov. 10, 2009 (JP) .................................. 2009-256883

(51) Int. Cl.
| | | |
|---|---|---|
| *A61M 16/04* | (2006.01) | |
| *B05D 1/18* | (2006.01) | |
| *B05D 3/00* | (2006.01) | |
| *B05D 7/00* | (2006.01) | |
| *C09D 143/02* | (2006.01) | |
| *A61L 17/14* | (2006.01) | |
| *A61L 29/08* | (2006.01) | |

(52) U.S. Cl.
CPC ............ *A61L 17/145* (2013.01); *A61L 29/085* (2013.01)
USPC .................. 526/274; 128/207.14; 128/207.15; 427/2.1; 427/2.3; 524/547

(58) Field of Classification Search
USPC .......... 526/274; 128/207.14, 207.15; 427/2.1, 427/2.3; 524/547
See application file for complete search history.

(56) References Cited

FOREIGN PATENT DOCUMENTS

| | | | |
|---|---|---|---|
| DK | WO2006074666 A1 | 7/2006 | |
| JP | 54-63025 A | 5/1979 | |
| JP | 3-39309 A | 2/1991 | |
| JP | 2003-102827 A | 4/2003 | |
| JP | 2005-6704 A | 1/2005 | |
| JP | 2006-238914 A | 9/2006 | |
| JP | WO2008023604 A1 | 2/2008 | |
| JP | 2009-261437 A | 11/2009 | |
| JP | 2009261437 | * 12/2009 | .............. A61L 29/00 |

OTHER PUBLICATIONS

Long et al. (Controlled biological response on blends of a phosphorylcholine-based copolymer with poly(butyl methacrylate); Biomaterials 24 (2003) 4115-4121).*
International Search Report for PCT/JP2010/002977 from the Japanese Patent Office completed on May 17, 2010 and mailed May 25, 2010 (4 pages).

* cited by examiner

*Primary Examiner* — Ling Choi
*Assistant Examiner* — Chun-Cheng Wang
(74) *Attorney, Agent, or Firm* — Pyprus Pte Ltd

(57) ABSTRACT

Disclosed is a respiration-assisting tube whereby tissue damages in vivo can be prevented and, as a result, inflammatory reactions and infections can be avoided. The respiration-assisting tube is developed based on the finding that adhesion of cells to a respiration-assisting tube can be inhibited by coating the respiration-assisting tube with a polymer containing 2-methacryloyloxyethyl phosphorylcholine (MPC). Also, the respiration-assisting tube is developed based on the finding that, by coating a respiration-assisting tube with a polymer containing MPC, mucosa peeling and tissue damages, which occur after using the respiration-assisting tube, can be prevented and, as a result, inflammatory reactions can be avoided.

9 Claims, 14 Drawing Sheets

Fig. 1
Fig. 1A
Cuffed Endotracheal Tube
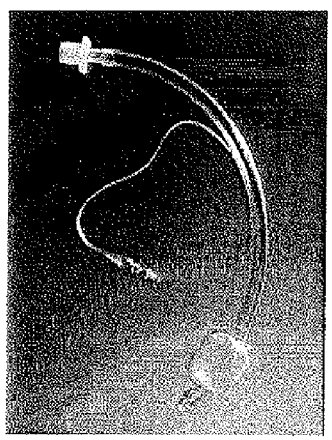
Fig. 1B
Cuffed Bronchial Tube
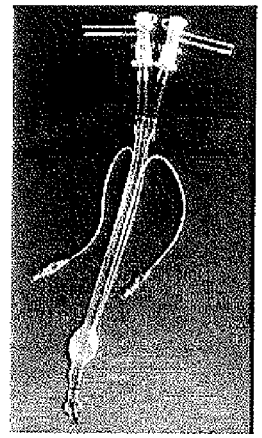
Fig. 1C
Cuffed Laryngeal Tracheal Tube
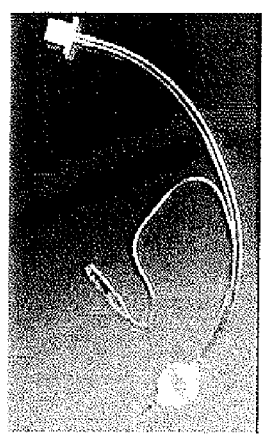
Fig. 1D
Cuffed Tracheostomy Tube
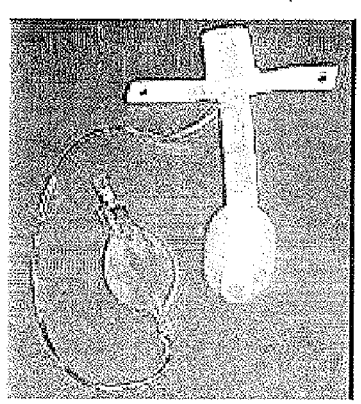
Fig. 1E
Esophagus Tube
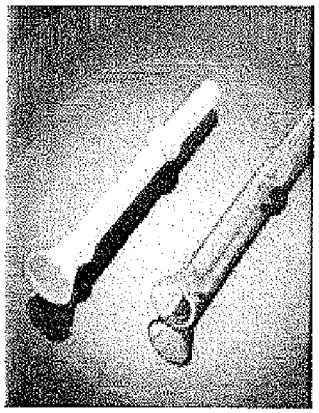

Fig. 3
Fig. 3A
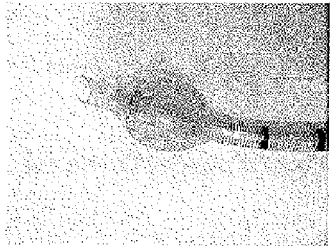
Fig. 3B
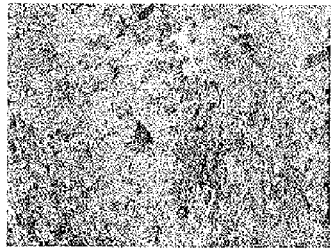
Fig. 3C
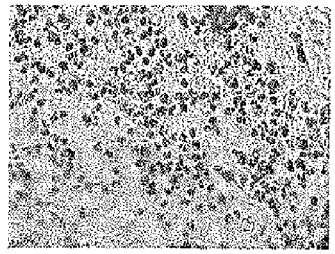
Fig. 3D
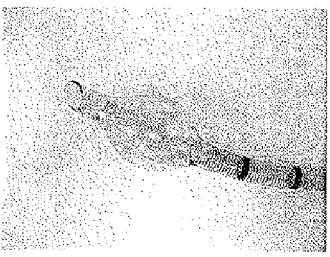
Fig. 3E
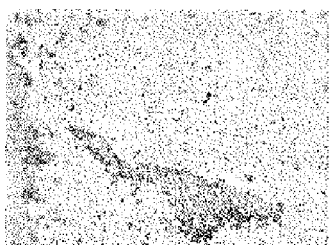
Fig. 3F
Fig. 3G
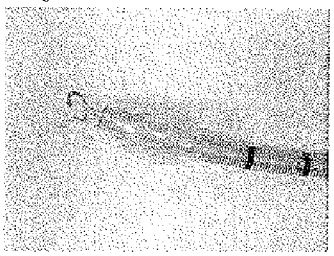
Fig. 3H
Fig. 3I
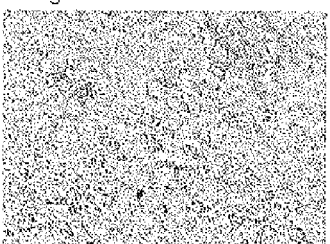

Fig. 4
Fig. 4A
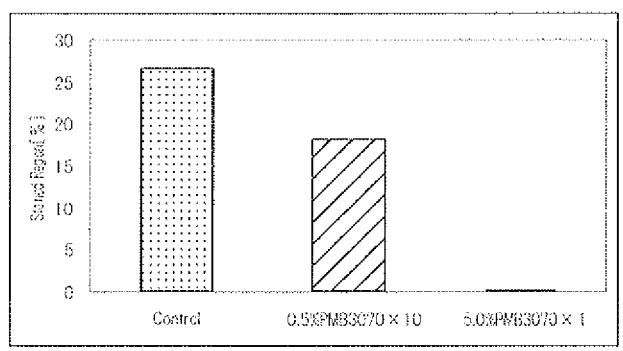
Fig. 4B
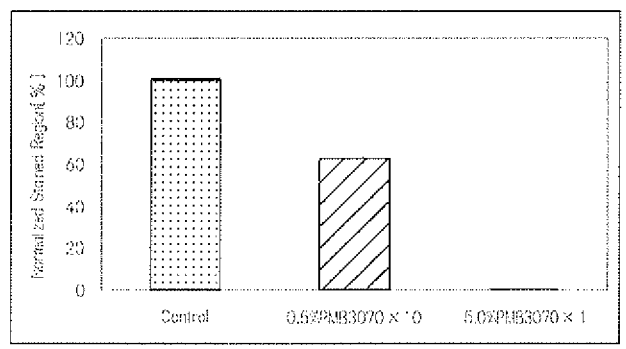

Fig. 5
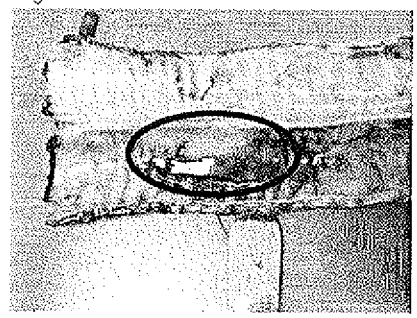
Fig. 5A
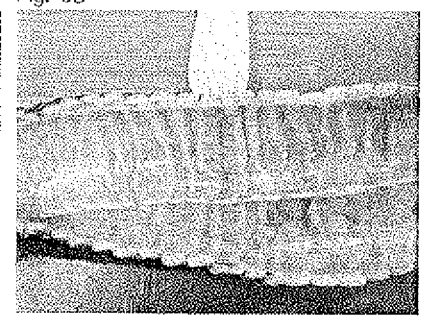
Fig. 5B

Fig. 6
Fig. 6A
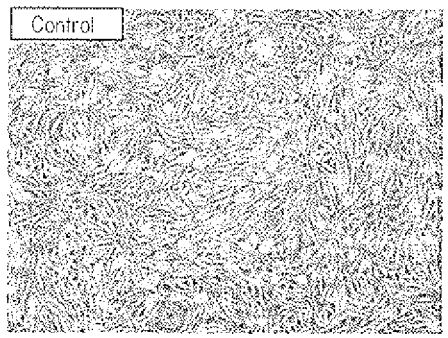
Fig. 6B
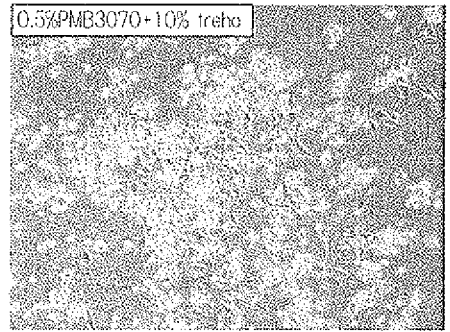
Fig. 6C
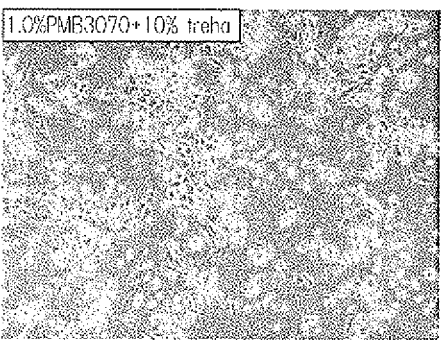
Fig. 6D
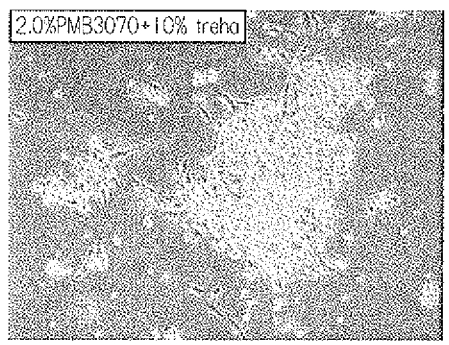
Fig. 6E
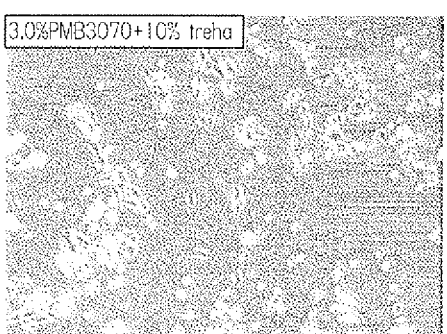
Fig. 6F
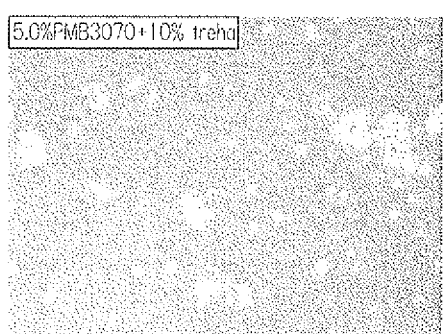

Fig. 7
Fig. 7A
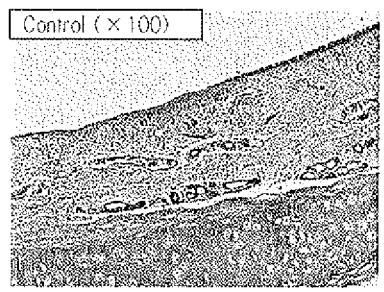
Control (×100)
Fig. 7B
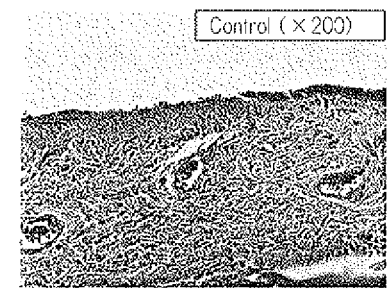
Control (×200)
Fig. 7C
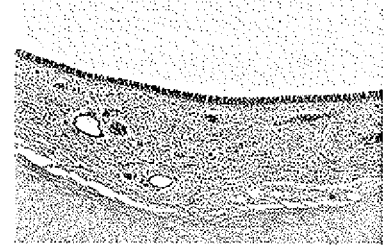
5.0%PMB3070 (×100)
Fig. 7D
5.0%PMB3070 (×200)

Fig.8
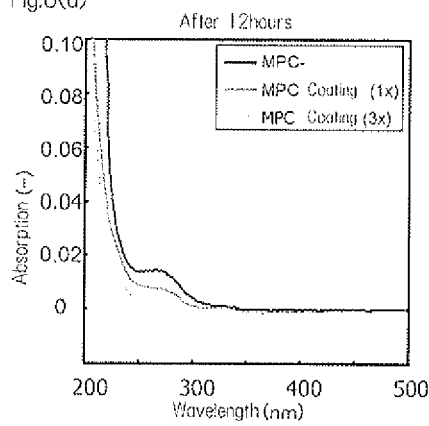
Fig.8(a)
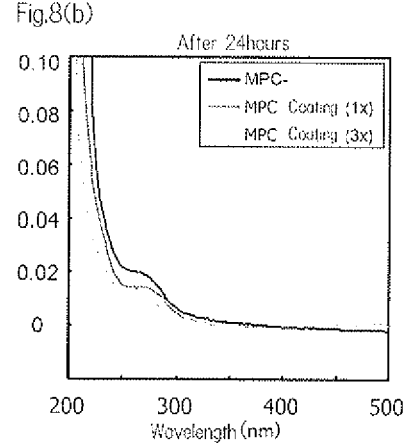
Fig.8(b)

Fig.10
Fig.10(a)
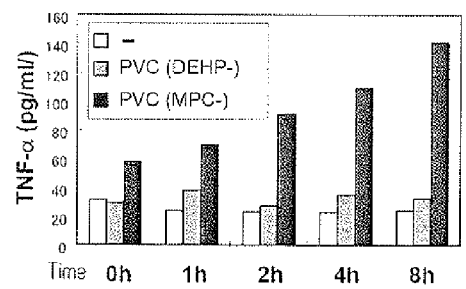
Fig.10(b)
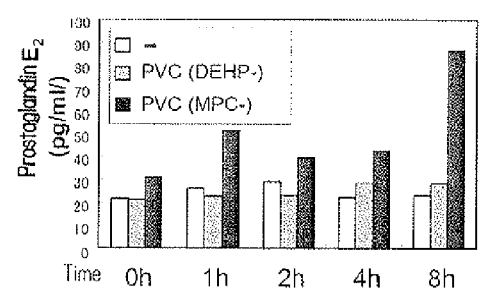

Fig.11
Fig.11(a)
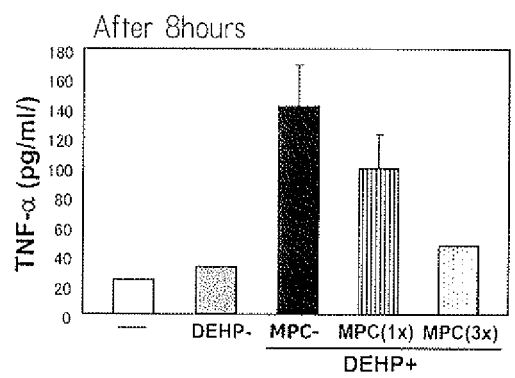
Fig.11(b)
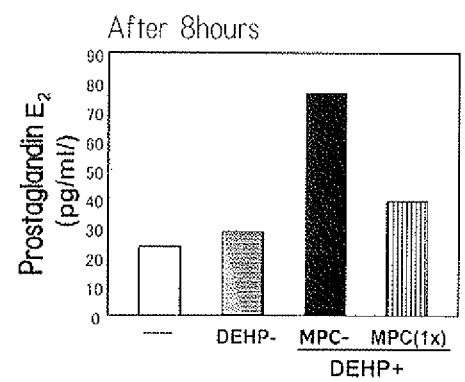

Fig.14
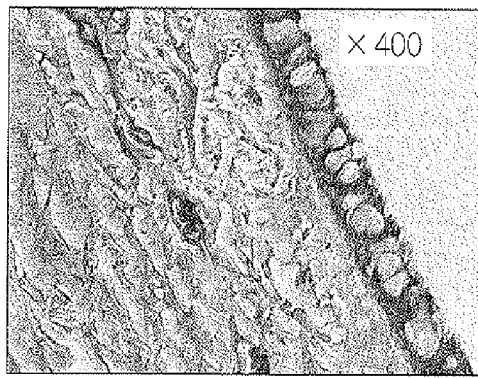
Fig.14(a)
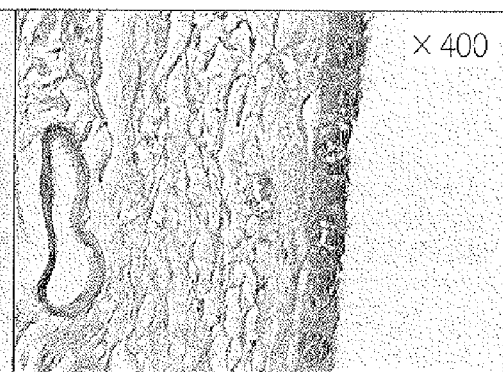
Fig.14(b)

RESIN PRODUCT FOR MEDICAL USE AND RESPIRATION-ASSISTING TUBE

TECHNICAL FIELD

This invention generally relates to a resin product for medical use that prevents the dissolution of plasticizer, a r respiratory support tube that has been coated with a polymer consisting 2-methacryloyloxyethyl phosphorylcholine (MPC).

BACKGROUND OF ART

Resin medical products are widely known to be used in various aspects of healthcare. However, there are problems in using resin medical products, especially made of PVC (poly vinyl chloride), that are known to cause inflammation, which is caused by unknown reasons, and other complications. An example of a resin medical product is a respiration-assisting tube.

Formerly, the respiration-assisting tube was widely used during a surgery. For example, Unexamined Japanese Patent Publication No. 2003-102827 discloses a tracheal tube that is manufactured from thermoplastics. As the tracheal tube disclosed in the Japanese Patent Publication No. 2003-102827 has low repulsion and thus the pain resulting from inserting the endotracheal tube can be reduced.

However, the respiration-assisting tube has high adhesiveness with the mucous tissue. Therefore when the respiration-assisting tube is removed, the cells on the tissue surface which are adhered onto the respiration-assisting tube will peel off. There will be difficulties, such as in expectoration of phlegm or an inflammation of the tracheal tissue after using the respiration-assisting tube.

The cells on the tracheal walls including the cilia will peel off when the respiration-assisting tube is removed. Thus the patient will not be able to discharge phlegm. Furthermore, there may be a problem where the phlegm flows backwards to the lungs causing pneumonia.

Patent Reference 1: Unexamined Patent Publication No. 2003-102827

SUMMARY OF THE INVENTION

Problems to be Resolved by the Invention

An object of this invention is to provide a resin medical product that can prevent an inflammation from occurring.

An other object of this invention is to provide a respiratory support tube (a respiration-assisting tube) that can prevent injuries to the tissues of a living body.

The other object of this invention is to provide a respiratory support tube that can prevent injuries to the tracheal tissues and the cilia from peeling off.

Means to Resolve the Problems

The first aspect of this invention is regarding a resin medical product that has polymer comprising repeating units consisting of phosphorylcholine derivative. That is, the inventors first discovered that using a resin medical product dissolves a small amount of plasticizer causing instances of inflammation. Thus based on the findings, the first aspect of the resin medical product of the invention, which comprises polymer comprising repeating units consisting of phosphorylcholine derivative, can prevent the dissolution of plasticizer that will prevent inflammation.

The first aspect of this invention is regarding a resin medical product that has a coating layer on the surface. The coating layer has polymer which comprises repeating units consisting of phosphorylcholine derivative represented by the following formula (A1).

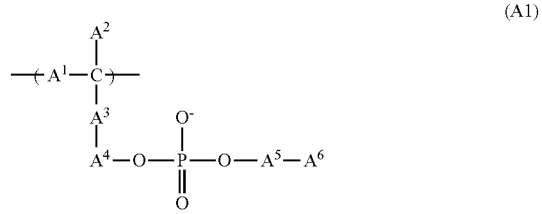

In the formula (A1),
$A^1$ represents a single bond, an optionally substituted $C_{1-10}$ alkylene group, or an optionally substituted $C_{2-10}$ alkenylene group.
$A^2$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group.
$A^3$ represents a group selected from the group represented in formula (A3).

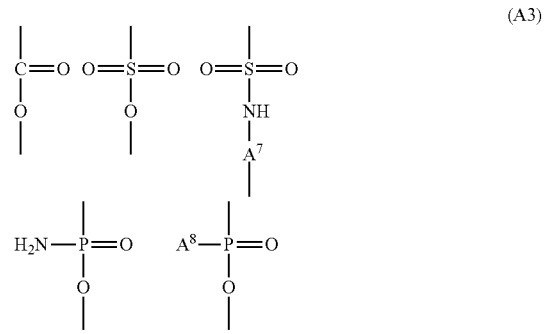

$A^4$ represents an optionally substituted $C_{1-10}$ alkylene group or an optionally substituted $C_{2-10}$ alkenylene group.
$A^5$ represents an optionally substituted $C_{1-10}$ alkylene group or an optionally substituted $C_{2-10}$ alkenylene group.
$A^6$ represents a group represented by the formula (A4).

In the formula (A3),
$A^7$ represents a single bond, an optionally substituted $C_{1-10}$ alkylene group, or an optionally substituted $C_{2-10}$ alkenylene group.
$A^8$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group.
In the formula (A4),
$A^9$-$A^{11}$, which may be identical or different, each represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group.

A preferred embodiment of the first aspect of this resin medical product invention is:

$A^1$ represents a $C_{1-10}$ alkylene group, or a $C_{1-10}$ alkenylene group;

$A^2$ represents a hydrogen atom, a halogen atom, a $C_{1-10}$ alkyl group, a $C_{2-10}$ alkenyl group, a $C_{2-10}$ alkynyl group, or a $C_{1-10}$ alkoxy group;

$A^4$ represents a $C_{1-10}$ alkylene group or a $C_{2-10}$ alkenylene group;

$A^5$ represents a $C_{1-10}$ alkylene group or a $C_{2-10}$ alkenylene group;

$A^7$ represents a single bond, a $C_{1-10}$ alkylene group, or a $C_{2-10}$ alkenylene group;

$A^8$ represents a hydrogen atom, a halogen atom, a $C_{1-10}$ alkyl group, a $C_{2-10}$ alkenyl group, a $C_{1-10}$ alkynyl group, or a $C_{1-10}$ alkoxy group; and $A^9$-$A^{11}$, which may be identical or different, each represents a hydrogen atom, a halogen atom, a $C_{1-10}$ alkyl group, a $C_{2-10}$ alkenyl group, a $C_{2-10}$ alkynyl group, or a $C_{1-10}$ alkoxy group.

A preferred embodiment of the first aspect of this resin medical product invention is:

$A^1$ represents a $C_{1-5}$ alkylene group;

$A^2$ represents a $C_{1-5}$ alkyl group;

$A^3$ represents a group that is represented by (—$CO_2$—);

$A^4$ represents a $C_{1-5}$ alkylene group;

$A^5$ represents a $C_{1-5}$; alkylene group;

$A^9$-$A^{11}$, which may be identical or different, each represents a hydrogen atom or a $C_{1-5}$ alkyl group.

A preferred embodiment of the first aspect of this resin medical product invention is:

$A^1$ represents a $C_{1-2}$ alkylene group;

$A^2$ represents a $C_{1-2}$ alkyl group;

$A^3$ represents a group that is represented as (—$CO_2$—);

$A^4$ represents a $C_{1-3}$ alkylene group;

$A^5$ represents a $C_{1-3}$ alkylene group;

$A^9$-$A^{11}$, which may be identical or different, each represents a $C_{1-2}$ alkyl group.

A preferred embodiment of the first aspect of this resin medical product invention are described as follows:

wherein $A^1$ represents a methylene group;

$A^2$ represents a methyl group;

$A^3$ represents a group that is represented as (—$CO_2$—);

$A^4$ represents an ethylene group;

$A^5$ represents an ethylene group;

$A^9$-$A^{11}$ represent a methyl group.

A preferred embodiment of the first aspect of this resin medical product invention is that the resin medical product comprises polyvinyl chloride as a main ingredient.

A preferred embodiment of the first aspect of this resin medical product invention is that the resin medical product comprises plasticizer.

A preferred embodiment of the first aspect of this resin medical product invention is:

the resin medical product is a medical bill tube that has a plastic part, a fluid-induced tube that has a plastic part, an apparatus for circulating blood outside body that has a plastic part, a blood collecting device that has a plastic part, a blood transfusion device that has a plastic part, an apparatus for transporting liquid that has a plastic part, a drug injector that has a plastic part, a suture that has a plastic part, or an apparatus for collecting urine that has a plastic part.

A preferred embodiment of the first aspect of this resin medical product invention is:

the medical plastic product comprises a pipe that has a plastic part, a bag that has a plastic part, a tube that has a plastic part, or a catheter that has a plastic part.

A preferred embodiment of the first aspect of this resin medical product invention is that the medical plastic product is a tube with a cuff, an endotracheal tube, a bronchial tube, a tracheostomy tube, a laryngeal tracheal tube, or an esophagus tube.

A preferred embodiment of the first aspect of this resin medical product invention is that the coating layer further comprises trehalose.

A preferred embodiment of the first aspect of this resin medical product invention is that the phosphorylcholine derivative is a co-polymer of phosphorylcholine derivative and hydrophilic monomer, the co-polymer is represented by formula (A2).

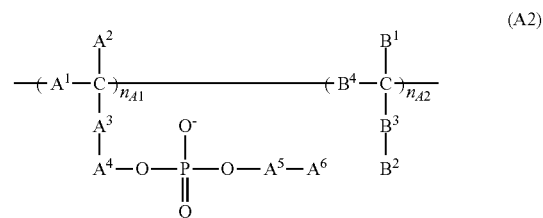

(A2)

In the formula (A2), $n_{A1}$ and $n_{A2}$, which is the same or different, represent the number from 20 to 2000.

$A^1$ represents a single bond, an optionally substituted $C_{1-10}$ alkylene group, or an optionally substituted $C_{2-10}$ alkenylene group.

$A^2$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group.

$A^3$ represents a group selected from the group represented by formula (A3).

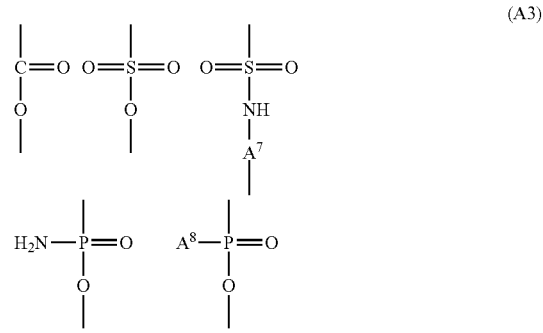

(A3)

$A^4$ represents an optionally substituted $C_{1-10}$ alkylene group or an optionally substituted $C_{2-10}$ alkenylene group.

$A^5$ represents an optionally substituted $C_{1-10}$ alkylene group or an optionally substituted $C_{2-10}$ alkenylene group.

$A^6$ represents a group represented by the formula (A4),

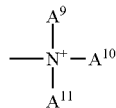

(A4)

In the formula (A3), $A^7$ represents a single bond, an optionally substituted $C_{1-10}$ alkylene group, or an optionally substituted $C_{2-10}$ alkenylene group.

$A^8$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group.

in the formula (A4), $A^9$-$A^{11}$, which may be identical or different, each represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group.

$B^1$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group.

$B^2$ represents an optionally substituted $C_{1-10}$ alkyl group, an optionally substituted $C_{2-10}$ alkenyl group, an optionally substituted $C_{2-10}$ alkynyl group, an optionally substituted $C_{1-10}$ alkoxy group, or a group that is represented as (—N($B^7B^8$)).

$B^3$ represents any one of the group represented in formula (A5), an optionally substituted $C_{1-8}$ alkylene group, an optionally substituted $C_{2-7}$ alkenylene group, an optionally substituted $C_{2-7}$ alkynylene group, or a group that is represented by (—COO—$B^9$—).

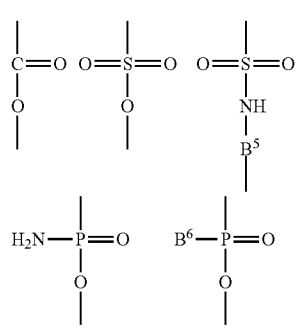

(A5)

$B^4$ represents a single bond, an optionally substituted $C_{1-10}$ alkylene group, or an optionally substituted $C_{2-10}$ alkenylene group.

In formula A5, $B^5$ represents a single bond, an optionally substituted $C_{1-10}$ alkylene group, an optionally substituted $C_{2-10}$ alkenylene group.

$B^6$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group.

$B^7$ and $B^8$, which may be identical or different, each represents a hydrogen atom, an optionally substituted $C_{1-10}$ alkyl group, an optionally substituted $C_{2-10}$ alkenyl group, an optionally substituted $C_{1-10}$ alkynyl group, or an optionally substituted $C_{1-10}$ alkoxy group.

$B^9$ represents a $C_{1-8}$ alkylene group, a $C_{2-7}$ alkenylene group, or a $C_{2-7}$ alkynylene group.

A preferred embodiment of the first aspect of this resin medical product invention is:

$A^1$ represents a $C_{1-10}$ alkylene group, or a $C_{2-10}$ alkenylene group;

$A^2$ represents a hydrogen atom, a halogen atom, a $C_{1-10}$ alkyl group, a $C_{2-10}$ alkenyl group, a $C_{2-10}$ alkynyl group, or a $C_{1-10}$ alkoxy group;

$A^4$ represents a $C_{1-10}$ alkylene group or a $C_{2-10}$ alkenylene group;

$A^5$ represents a $C_{1-10}$ alkylene group or a $C_{2-10}$ alkenylene group;

$A^7$ represents a single bond, a $C_{1-10}$ alkylene group, or a $C_{2-10}$ alkenylene group;

$A^8$ represents a hydrogen atom, a halogen atom, a $C_{1-10}$ alkyl group, a $C_{2-10}$ alkenyl group, a $C_{2-10}$ alkynyl group, or a $C_{1-10}$ alkoxy group;

$A^9$-$A^{11}$, which may be identical or different, each represents a hydrogen atom, a halogen atom, a $C_{1-10}$ alkyl group, a $C_{2-10}$ alkenyl group, a $C_{1-10}$ alkynyl group, or a $C_{1-10}$ alkoxy group;

$B^1$ represents a hydrogen atom, a halogen atom, a $C_{1-10}$ alkyl group, a $C_{2-10}$ alkenyl group, a $C_{2-10}$ alkynyl group, or a $C_{1-10}$ alkoxy group;

$B^2$ represents a $C_{1-10}$ alkyl group, a $C_{2-10}$ alkenyl group, a $C_{2-10}$ alkynyl group, or a $C_{1-10}$ alkoxy group;

$B^3$ represents any one of the group represented in formula (A5), $B^4$ represents a single bond, a $C_{1-10}$ alkylene group, or a $C_{2-10}$ alkenylene group;

$B^5$ represents a single bond, a $C_{1-10}$ alkylene group, or a $C_{2-10}$ alkenylene group; and $B^6$ represents a hydrogen atom, a halogen atom, a $C_{1-10}$ alkyl group, a $C_{2-10}$ alkenyl group, a $C_{2-10}$ alkynyl group, or a $C_{1-10}$ alkoxy group.

A preferred embodiment of the first aspect of this resin medical product invention is:

$A^1$ represents a $C_{1-5}$ alkylene group;

$A^2$ represents a $C_{1-5}$ alkyl group;

$A^3$ represents a group that is represented as (—$CO_2$—);

$A^4$ represents a $C_{1-5}$ alkylene group;

$A^5$ represents a $C_{1-5}$ alkylene group;

$A^9$-$A^{11}$, which may be identical or different, each represents a hydrogen atom, or a $C_{1-5}$ alkyl group;

$B^1$ represents a $C_{1-5}$ alkyl group;

$B^2$ represents a $C_{2-7}$ alkyl group;

$B^3$ represents a group that is represented as (—$CO_2$—); and $B^4$ represents a $C_{1-5}$ alkylene group.

A preferred embodiment of the first aspect of this resin medical product invention is:

$A^1$ represents a $C_{1-2}$ alkylene group;

$A^2$ represents a $C_{1-2}$ alkyl group;

$A^3$ represents a group that is represented as (—$CO_2$—);

$A^4$ represents a $C_{1-3}$ alkylene group;

$A^5$ represents a $C_{1-3}$ alkylene group;

$A^9$-$A^{11}$, which may be identical or different, each represents a $C_{1-2}$ alkyl group;

$B^1$ represents a $C_{1-2}$ alkyl group;

$B^2$ represents a $C_{3-5}$ alkyl group;

$B^3$ represents a group that is represented as (—$CO_2$—); and $B^4$ represents a $C_{1-2}$ alkylene group.

A preferred embodiment of the first aspect of this resin medical product invention is:

$A^1$ represents a methylene group;
$A^2$ represents a methyl group;
$A^3$ represents a group that is represented as (—$CO_2$—);
$A^4$ represents an ethylene group;
$A^5$ represents an ethylene group;
$A^9$-$A^{11}$ represent a methyl group;
$B^1$ represents a methyl group;
$B^2$ represents a butyl group;
$B^3$ represents a group that is represented as (—$CO_2$—); and
$B^4$ represents a methylene group.

A preferred embodiment of the first aspect of this resin medical product invention is:

$A^1$ represents a $C_{1-10}$ alkylene group, or a $C_{2-10}$ alkenylene group;
$A^2$ represents a hydrogen atom, a halogen atom, a $C_{1-10}$ alkyl group, a $C_{2-10}$ alkenyl group, a $C_{2-10}$ alkynyl group, or a $C_{1-10}$ alkoxy group;
$A^4$ represents a $C_{1-10}$ alkylene group or a $C_{2-10}$ alkenylene group;
$A^5$ represents a $C_{1-10}$ alkylene group or a $C_{2-10}$ alkenylene group;
$A^7$ represents a single bond, a $C_{1-10}$ alkylene group, or a $C_{2-10}$ alkenylene group;
$A^8$ represents a hydrogen atom, a halogen atom, a $C_{1-10}$ alkyl group, a $C_{2-10}$ alkenyl group, a $C_{2-10}$ alkynyl group, or a $C_{1-10}$ alkoxy group;
$A^9$-$A^{11}$, which may be identical or different, each represents a hydrogen atom, a halogen atom, a $C_{1-10}$ alkyl group, a $C_{2-10}$ alkenyl group, a $C_{2-10}$ alkynyl group, or a $C_{1-10}$ alkoxy group;
$B^1$ represents a hydrogen atom, a halogen atom, a $C_{1-10}$ alkyl group, a $C_{2-10}$ alkenyl group, a $C_{2-10}$ alkynyl group, or a $C_{1-10}$ alkoxy group;
$B^2$ represents a group that is represented as (—$N(B^7B^8)$);
$B^3$ represents a $C_{1-8}$ alkylene group, a $C_{2-7}$ alkenylene group, a $C_{2-7}$ alkynylene group, or a group that is represented as (—COO—$B^9$—);
$B^4$ represents a single bond, a $C_{1-10}$ alkylene group, a $C_{2-10}$ alkenylene group;
$B^7$ and $B^8$, which may be identical or different, each represents a hydrogen atom, a $C_{1-10}$ alkyl group, a $C_{2-10}$ alkenyl group, a $C_{2-10}$ alkynyl group, or a $C_{1-10}$ alkoxy group; and
$B^9$ represents a $C_{1-8}$ alkylene group.

A preferred embodiment of the first aspect of this resin medical product invention is:

$A^1$ represents a $C_{1-5}$ alkylene group;
$A^2$ represents a $C_{1-5}$ alkyl group;
$A^3$ represents a group that is represented as (—$CO_2$—);
$A^4$ represents a $C_{1-5}$ alkylene group;
$A^5$ represents a $C_{1-5}$ alkylene group;
$A^9$-$A^{11}$, which may be identical or different, each represents a $C_{1-5}$ alkyl group;
$B^1$ represents a $C_{1-5}$ alkyl group;
$B^2$ represents a group that is represented as (—$N(B^7B^8)$);
$B^3$ represents a $C_{1-8}$ alkylene group;
$B^4$ represents a $C_{1-5}$ alkylene group; and
$B^7$ and $B^8$, which may be identical or different, each represents a hydrogen atom, or a $C_{1-5}$ alkyl group.

A preferred embodiment of the first aspect of this resin medical product invention is:

$A^1$ represents a $C_{1-2}$ alkylene group;
$A^2$ represents a $C_{1-2}$ alkyl group;
$A^3$ represents a group that is represented as (—$CO_2$—);
$A^4$ represents a $C_{1-3}$ alkylene group;
$A^5$ represents a $C_{1-3}$ alkylene group;
$A^9$-$A^{11}$, which may be identical or different, each represents a $C_{1-2}$ alkyl group;
$B^1$ represents a $C_{1-2}$ alkyl group;
$B^2$ represents a group that is represented as (—$N(B^7B^8)$);
$B^3$ represents a $C_{2-5}$ alkylene group;
$B^4$ represents a $C_{1-2}$ alkylene group; and
$B^7$ and $B^8$, which may be identical or different, each represents a hydrogen atom, or a $C_{1-2}$ alkyl group.

A preferred embodiment of the first aspect of this resin medical product invention is:

$A^1$ represents a methylene group;
$A^2$ represents a methyl group;
$A^3$ represents a group that is represented as (—$CO_2$—);
$A^4$ represents an ethylene group;
$A^5$ represents an ethylene group;
$A^9$-$A^{11}$ represent a methyl group
$B^1$ represents a methyl group;
$B^2$ represents an amino group;
$B^3$ represents a $C_{2-5}$ alkylene group; and
$B^4$ represents a methylene group.

The resin medical product mentioned above can make use of the appropriate combination of desirable elements. MPC is a preferred example of the phosphorylcholine derivative and is represented by the following formula (A1).

A preferred usage embodiment of the first aspect of this resin medical product invention pertains to a method for preventing plasticizer for resin medical product from dissolving. The method comprises a step of forming a coating layer on the surface of the resin medical product. The coating layer which has polymer comprising repeating units consisting of phosphorylcholine derivative and the unit is represented by the following formula (A1).

$$\begin{array}{c} A^2 \\ | \\ -(A^1-C)- \\ | \\ A^3 \quad O^- \\ | \\ A^4-O-P-O-A^5-A^6 \\ \| \\ O \end{array} \quad (A1)$$

In the formula (A1), $A^1$ represents a single bond, an optionally substituted $C_{1-10}$ alkylene group, or an optionally substituted $C_{2-10}$ alkenylene group;

$A^2$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group;

$A^3$ represents a group selected from the group represented in formula (A3);

$$\begin{array}{ccc} | & | & | \\ C=O & O=S=O & O=S=O \\ | & | & | \\ O & O & NH \\ | & | & | \\ & & A^7 \\ & & | \end{array} \quad (A3)$$

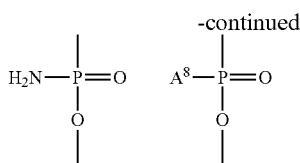

$A^4$ represents an optionally substituted $C_{1-10}$ alkylene group or an optionally substituted $C_{2-10}$ alkenylene group;

$A^5$ represents an optionally substituted $C_{1-10}$ alkylene group or an optionally substituted $C_{2-10}$ alkenylene group; and $A^6$ represents a group selected from the group represented in formula (A4).

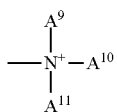

(A4)

In the formula (A3), $A^7$ represents a single bond, an optionally substituted $C_{1-10}$ alkylene group, or an optionally substituted $C_{2-10}$ alkenylene group;

$A^8$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group, and wherein in the formula (A4), $A^9$-$A^{11}$, which may be identical or different, each represent a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group.

The method to prevent the dissolution of plasticizer for the resin medical product makes use of the appropriate combination of desirable elements of the resin medical product.

A preferred embodiment of the above method is that the phosphorylcholine derivative is co-polymer of a derivative of phosphorylcholine and a hydrophobic monomer, the co-polymer is represented in formula (A2):

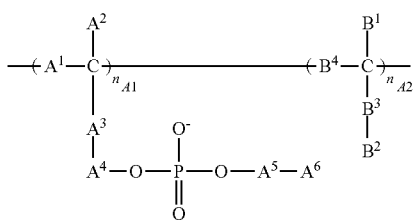

(A2)

In the formula (A2), $n_{A1}$ and $n_{A2}$ represent a number from 20 to 2000 that may be the same or different, $A^1$ represents a single bond, an optionally substituted $C_{1-10}$ alkylene group, or an optionally substituted $C_{2-10}$ alkenylene group;

$A^2$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group;

$A^3$ represents a group selected from the group represented in formula (A3);

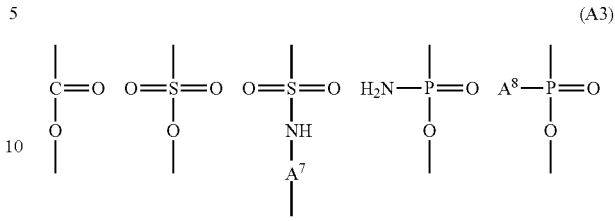

(A3)

$A^4$ represents an optionally substituted $C_{1-10}$ alkylene group or an optionally substituted $C_{2-10}$ alkenylene group;

$A^5$ represents an optionally substituted $C_{1-10}$ alkylene group or an optionally substituted $C_{2-10}$ alkenylene group; and $A^6$ represents a group selected from the group represented in formula (A4),

(A4)

In the formula (A3), $A^7$ represents a single bond, an optionally substituted $C_{1-10}$ alkylene group, or an optionally substituted $C_{2-10}$ alkenylene group;

$A^8$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group, and wherein in the formula (A4), $A^9$-$A^{11}$, which may be identical or different, each represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group, $B^1$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group;

$B^2$ represents an optionally substituted $C_{1-10}$ alkyl group, an optionally substituted $C_{2-10}$ alkenyl group, an optionally substituted $C_{2-10}$ alkynyl group, an optionally substituted $C_{1-10}$ alkoxy group, or a group that is represented as (—N($B^7B^8$));

$B^3$ represents any one of the group represented in formula (A5), an optionally substituted $C_{1-8}$ alkylene group, an optionally substituted $C_{2-7}$ alkenylene group, an optionally substituted $C_{2-7}$ alkynylene group, or a group that is represented as (—COO—$B^9$—).

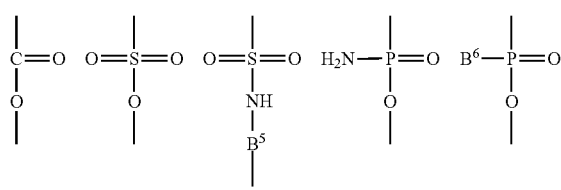

(A5)

$B^4$ represents a single bond, an optionally substituted $C_{1-10}$ alkylene group, an optionally substituted $C_{2-10}$ alkenylene group.

In formula A5, $B^5$ represents a single bond, an optionally substituted $C_{1-10}$ alkylene group, an optionally substituted $C_{2-10}$ alkenylene group;

$B^6$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group;

$B^7$ and $B^8$, which may be identical or different, each represents a hydrogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group; and $B^9$ represents a $C_{1-8}$ alkylene group, a $C_{2-7}$ alkenylene group, or a $C_{2-7}$ alkynylene group.

The method to prevent the dissolution of plasticizer for the resin medical product makes use of the appropriate combination of desirable elements of the resin medical product.

The second aspect of this invention relates to a respiratory support tube. This respiratory support tube is a subordinate concept of the resin medical product mentioned above. In other words, this respiratory support tube can not only prevent the dissolution of plasticizer, but also achieve the effects pertaining to the second aspect of this invention.

The second aspect of this invention is based on the findings that since the respiratory support tube has a coating layer, wherein the coating layer is a polymer comprising 2-methacryloyloxy ethyl phosphorylcholine (hereinafter, also known as "MPC), the adhesion of the respiratory support tube to the cells can be restrained. Furthermore as based on the findings, this invention can prevent injuries such as tissue damages and cilia detachment when the respiratory support tube is removed as the respiratory support tube has a coating layer, wherein the coating layer is a polymer comprising MPC.

The second aspect of this invention is regarding a respiratory support tube that has a coating later, wherein the coating layer is a polymer comprising MPC. As described in the working examples below, the situation where the cells get detached can be prevented when the respiratory support tube is used and removed, as the respiratory support tube has a polymer coating layer comprising MPC. As a result, inflammatory reactions can be avoided by using the respiratory support tube. Furthermore as described in the embodiments below, this respiratory support tube invention will not injure the biological tissues when it is attached and removed. Because of this, this respiratory support tube invention can prevent the situation whereby the cilia on the tracheal walls will peel off. Therefore, pneumonia can be avoided when this respiratory support tube invention is used.

A preferred embodiment of the second aspect of this invention is a respiratory support tube having a coating layer on the surface. The coating layer of the respiratory support tube is co-polymer of 2-methacryloyloxy ethyl phosphorylcholine of formula and hydrophobic monomer, the co-polymer is represented in formula (I):

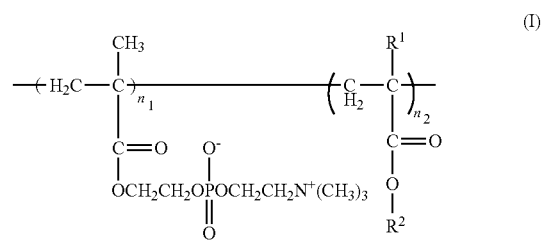

here in formula (I), $n_1$ and $n_2$ represent an integer from 20 to 1500 that may be the same or different. $R^1$ represents H, or $C_{1-3}$ alkyl group. $R^2$ represents $C_{4-15}$ alkyl group, $C_{4-15}$ alkenyl group, or $C_{4-15}$ alkynyl group. As mentioned later, a hydrophobic group of the copolymer binds to a hydrophobic group on the surface of a respiratory assistance tube with hydrophobic interaction. Thus the coating layer becomes bilayer membrane like cell membrane. This coating layer shows low adhesiveness to cells or proteins. Thus when a respiratory assistance tube comprising a coating layer including MPC and a hydrophobic monomer is used, tissues of a living body is not injured after use of the respiratory assistance tube. Thus inflammatory response by using a respiratory assistance tube may be avoided.

A preferred embodiment of the invention is that the coating layer of a respiratory assistance tube comprises a copolymer including 2-methacryloyloxyethylphosphorylcholine (MPC) and a basic monomer. This copolymer is shown in the following chemical formula (II).

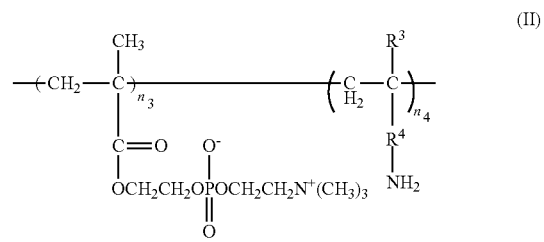

In chemical formula (II), $n_3$ and $n_4$ may be equal or different and indicate integers ranging from 20 to 1500. $R^3$ represents a hydrogen atom or an alkyl group having 1 to 3 carbon atoms. $R^4$ represents an alkylene group having 1 to 8 carbon atoms, an alkenylene group having 2 to 7 carbon atoms, an alkynyl group having 2 to 7 carbon atoms or —COO—$R^5$—, wherein $R^5$ represents an alkylene group having 1 to 8 carbon atoms, an alkenylene group having 2 to 7 carbon atoms or an alkynyl group having 2 to 7 carbon atoms. As mentioned later, a basic group of copolymer binds to a carboxyl group or a glurysyl group on the surface of a respiratory assistance tube with ionic interaction. Thus the coating layer becomes bilayer membrane like cell membrane. This coating layer shows low adhesiveness to cells or proteins of a living body. Thus when a respiratory assistance tube comprising a coating layer including MPC and a basic monomer is used, tissues of a living body is not injured after use of the respiratory assistance tube. Thus inflammatory response by using a respiratory assistance tube may be avoided.

A preferred embodiment of the second aspect of the invention is the above respiratory assistance tube, wherein thickness of the coating layer is $1 \times 10^0$ to $1 \times 10^4$ µm. By preparing this coating layer, injuries of tissues of a living body may be prevented when a respiratory assistance tube is used, attached or removed. Thus inflammatory response by using a respiratory assistance tube may be avoided.

A preferred embodiment of the second aspect of the invention is that the coating layer of the respiratory assistance tube further includes trehalose. As mentioned in later embodiment, a coating layer including MPC and trehalose may decrease adhesion of cells. Thus a respiratory assistance tube in the invention may prevent detachment of cells of tissue of a living body by using the respiratory assistance tube. Thus inflammatory response by using a respiratory assistance tube may be avoided.

A preferred embodiment of the second aspect of the invention is that the respiratory assistance tube of the respiratory assistance tube is one of an endotracheal tube, a bronchial tube, a tracheotomy tube, a laryngotracheal tube and an esophageal tube. Furthermore, the respiratory assistance tube may be a tube that has a cuff. As explained in the following working experiment, a respiratory assistance tube of the present invention does not peel off cells of tissue of a living body when the respiratory assistance tube is attached or removed. Thus the respiratory assistance can prevent inflammatory response.

The third aspect of the invention relates to a method for coating a respiratory assistance tube. The process of the invention comprises a step of coating respiratory assistance tube with a coating liquid that comprises 0.01 to 50 wt % of polymer. The polymer comprises 2-metacryloyloxyethyl phosphorylcholine (MPC). As explained in the following working examples, a respiratory assistance tube made with the method shows low adhesiveness to cells. Thus the respiratory assistance tube made by the method of the present invention does not peel off cells of tissue of a living body when the respiratory assistance tube is attached or removed. Thus the respiratory assistance can prevent inflammatory response.

A preferred embodiment of the third aspect is that a coating process comprises an immersion process to immerse a respiratory assistance tube into the coating liquid and a drying process to dry the respiratory assistance tube immersed in the immersion process. The immersion process and the drying process are repeated 2 to 20 times. As mentioned in later embodiment, a respiratory assistance tube made with this process shows low adhesiveness to cells. Thus a respiratory assistance tube in the invention does not peel off mucosal cells of trachea after the respiratory assistance tube is removed. Thus inflammatory response by using the respiratory assistance tube may be avoided.

Effects of the Invention

According to this invention, a resin medical product which may suppress an occurrence of inflammation can be provided. Particularly according to this invention, both sides of the inner and outer walls of the respiratory support tube that comprises endotracheal tube can form a biofilm layer. Because of the hydrophilicity of the biofilm layer, it can effectively prevent a situation whereby phlegm and others may grow into capsules and enter the lungs causing pneumonia and other complications. Thus according to this invention, the occurrence of infectious diseases can be prevented because of the biofilm layer formed on the inner and outer walls of the respiratory support tube.

According to this invention, a respiratory assistance tube which may prevent injuries of tissues of a living body may be provided. According to this invention, injuries of tissues of a living body may be prevented, so inflammatory response may be avoided. Particularly according to this invention, a biofilm layer can be formed on the outer walls of the respiratory assistance tube. As this biofilm layer is relatively smooth, the coefficient of friction is lower than that of the tube. For this reason, the respiratory assistance tube that comprises a biofilm layer is relatively easy inserted into the trachea of patients. Moreover, the respiration assistance tube is moved around in the trachea once the respiration assistance tube has been inserted into the trachea of patients. In this case, the respiration assistance tube and the patient's tissues will cause friction. According to this invention, damages to the biological tissues can be prevented as the outer walls of the respiratory assistance tube can be covered with a smooth layer of biofilm that reduces friction. Because of the MPC coating in this invention, the damage to the respiratory tract and the vocal cords can be mitigated by reducing the frictional resistance to the airway mucosa, thereby suppressing the bleeding from these biological tissues. According to this invention, a respiratory assistance tube which may prevent injuries of cilia may be provided. According to the invention, injuries of tissues of a living body may be prevented, so pneumonia may be avoided. According to this invention, because there are no damages to the ciliated cells in the respiratory tract, the expectoration of secretions that comprises bacteria from sputum or from the lungs will not be inhibited and thus can restrain the onset of pneumonia.

BRIEF DESCRIPTION OF THE DRAWINGS

FIG. 1 shows photographs indicating examples of respiratory assistance tube in the invention. FIG. 1A shows a photograph of a cuffed endotracheal tube, FIG. 1B shows a photograph of a cuffed bronchial tube, FIG. 1C shows a photograph of a cuffed tracheotomy tube, FIG. 1D shows a photograph of a cuffed laryngotracheal tube and FIG. 1E shows a photograph of an esophageal tube.

FIG. 3 shows photographs of the cuff stained with Hematoxylin. FIGS. 3A to 3C show photographs of a cuff of a tube without PMB3070 coating. FIGS. 3D to 3F show photographs of a cuff of a tube coated with 0.5 wt % PMB3070 10 times (0.5% PMB3070×10). FIGS. 3G to 3I show photographs of a cuff of a tube coated with 5.0 wt % PMB3070 once (5.0% PMB3070×1). FIGS. 3A, 3D and 3G show photographs of a cuff at 1-fold magnification. FIGS. 3B, 3E and 3H show microscopic photographs of a cuff at 50-fold magnification. FIGS. 3C, 3F and 3I show microscopic photographs of a cuff at 400-fold magnification.

FIG. 4 shows a graph of ratio determined by graphic software after digitizing of portion stained with Hematoxylin.

FIG. 5 shows a photograph of a degree of injuries of trachea after insertion of a respiratory assistance tube.

FIG. 6 shows a photograph indicating that coating with PMB3070 and trehalose decreases adhesiveness of cells. FIG. 6A shows a photograph of a control dish (a cell culture dish without coating), FIG. 6B to 6F show photographs of adhesiveness of cells to dishes coated with PMB3070 and trehalose.

FIG. 7 shows a photograph indicating of inhibitory effect of injuries of tracheal mucosa by an endotracheal tube coated with PMB3070. FIGS. 7A and 7B show a control, indicating tracheal tissues when a tube without coating is used, at 100- and 200-fold magnification, respectively. FIGS. 7C and 7D show tracheal tissues when a tube coated with PMB3070 is used, at 100- and 200-fold magnification, respectively.

FIG. 8 are graphs that show the light absorption spectrum measurement results to demonstrate the potential in preventing the dissolution of plasticizer by the MPC coating. FIG. 8A shows the light absorption spectrum of the immersion fluid after 12 hours from the start of immersion. FIG. 8B shows the light absorption spectrum of the immersion fluid after 24 hours from the start of immersion.

FIG. 10 are graphs that show the effects of suppressing the inflammatory response of DEHP that is released from PVC of the MPC coating. FIG. 10A shows the measurement results of TNT-α (alpha) culture medium. FIG. 10B shows the measurement results of prostaglandin E2 (PGE2) culture medium.

FIG. 11 are graphs that show the effects of suppressing the inflammatory response of DEHP that is released from PVC that was immersed in medium for 8 hours. FIG. 11A shows the measurement results of TNF-α (alpha) culture medium. FIG. 11B shows the measurement results of prostaglandin E2 (PGE2) culture medium.

FIG. 12A shows the HE dyeing results of a PVC respiratory support tube (MPC–) that has not been coated with MPC. FIG. 12B shows the magnified image of FIG. 12A. FIG. 12C shows the HE dyeing results of a PVC respiratory support tube (133 MPC coating) that has been coated with MPC. FIG. 12D shows the magnified image of FIG. 12C.

FIG. 13A shows the PAS dyeing results of a PVC respiratory support tube (MPC–) that has not been coated with MPC. FIG. 13B shows the magnified image of FIG. 13A. FIG. 13C shows the PAS dyeing results of a PVC respiratory support tube (1×MPC coating) that has been coated with MPC. FIG. 13D shows the magnified image of FIG. 13C.

FIG. 14 are photographs that show the peeling of mucosal cells of trachea as shown by the dyeing of HE and PAS at the surrounding tissues. FIG. 14A shows the HE dyeing results of a PVC respiratory support tube (MPC–) that has not been coated with MPC. FIG. 14B shows the PAS dyeing results of a PVC respiratory support tube (MPC–) that has not been coated with MPC.

BEST MODE FOR CARRYING OUT THE INVENTION

Figure 2:
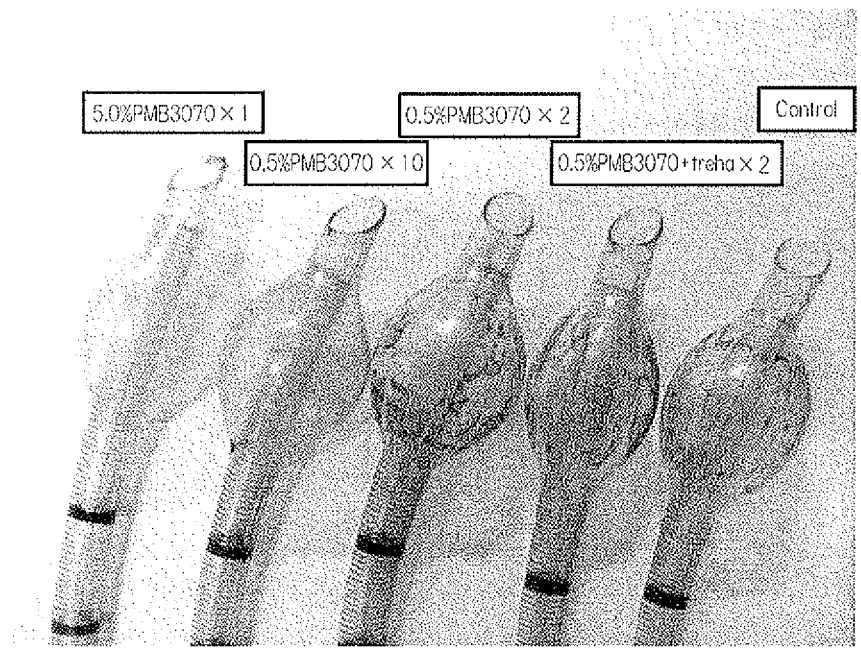
FIG. 2 shows a photograph of cuffed endotracheal tubes stained with Hematoxylin.

The first aspect of this resin medical product of the present invention is regarding a resin medical product that has a coating layer on the surface. The term "a resin medical product" is a medical product that has plastic parts. It is preferred that the resin medical product of the invention comprises a plastic part that touches the patient's organs.

The "coating layer" is referring to the surface of the resin part that may use another resin to form layers onto the surface. Thus when the resin medical product is manufactured, the other resin containing the polymer of this invention as explained below may also be on the surface.

The coating layer has a coating layer on the surface thereof. The coating layer has polymer (polymer 1 of this invention) comprising repeating units consisting of a phosphorylcholine derivative which is represented by the following formula (A1). As demonstrated in the working examples, polymer 1 of this invention can effectively prevent the dissolution of plasticizer.

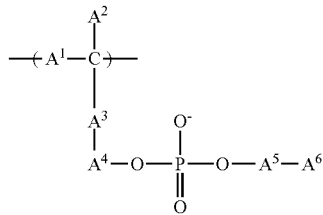

(A1)

Examples of the average number of molecular weight of polymer 1 are $1 \times 10^4$ to $5 \times 10^5$, preferably $3 \times 10^4$ to $4 \times 10^5$, more preferably $5 \times 10^4$ to $3 \times 10^5$, and $1 \times 10^5$ to $3 \times 10^5$ which is further preferred. Such polymers may be made by using known methods or may use what is available commercially. Particularly, an example of polymer 1 is a widely synthesized MPC polymer. Thus, polymer 1 of this invention can be produced by applying the known methods of producing MPC polymer.

$A^1$ represents a single bond, an optionally substituted $C_{1-10}$ alkylene group, or an optionally substituted $C_{2-10}$ alkenylene group. A preferred example of $A^1$ is an unsubstituted $C_{1-10}$ alkylene group, or an unsubstituted $C_{2-10}$ alkenylene group. A further preferred example of $A^1$ is $C_{1-5}$ alkylene group, more preferably methylene group or ethylene group.

$A^2$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group. A preferred example of $A^2$ is a hydrogen atom, a halogen atom, an unsubstituted $C_{1-10}$ alkyl group, an unsubstituted $C_{2-10}$ alkenyl group, an unsubstituted $C_{2-10}$ alkynyl group, or an unsubstituted $C_{1-10}$ alkoxy group. A further preferred example of $A^2$ is $C_{1-5}$ alkyl group, more preferably methyl group or ethyl group.

$A^3$ represents a group selected from the group represented in formula (A3). $A^3$ preferably represents a group that is represented in the formula ($—CO_2—$).

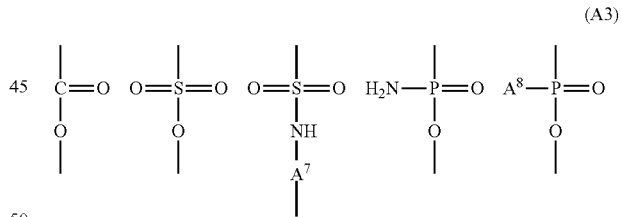

(A3)

$A^7$ represents a single bond, an optionally substituted $C_{1-10}$ alkylene group, or an optionally substituted $C_{2-10}$ alkenylene group. $A^7$ preferably represents a single bond, a non substituted $C_{1-10}$ alkylene group, or a non substituted $C_{2-10}$ alkenylene group. More preferred $A^7$ is a single bond or a $C_{1-5}$ alkylene group. Further preferred $A^7$ is a methylene group.

$A^8$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group. $A^8$ preferably represents a hydrogen atom, a halogen atom, a non substituted $C_{1-10}$ alkyl group, a non substituted $C_{2-10}$ alkenyl group, a non substituted $C_{2-10}$ alkynyl group, or a non substituted $C_{1-10}$ alkoxy group. More preferred $A^8$ is a hydrogen atom or a $C_{1-5}$ alkyl group. Further preferred $A^8$ is a methyl group.

$A^4$ represents an optionally substituted $C_{1-10}$ alkylene group or an optionally substituted $C_{2-10}$ alkenylene group. $A^4$ preferably represents a non substituted $C_{1-10}$ alkylene group or a non substituted $C_{2-10}$ alkenylene group. More preferred $A^4$ is a $C_{1-3}$ alkylene group.

$A^5$ represents an optionally substituted $C_{1-10}$ alkylene group or an optionally substituted $C_{2-10}$ alkenylene group. $A^5$ preferably represents a non substituted $C_{1-10}$ alkylene group or a non substituted $C_{2-10}$ alkenylene group. More preferred $A^5$ is a $C_{1-3}$ alkylene group.

$A^6$ represents a group represented by the formula (A4).

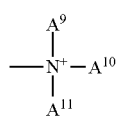

(A4)

In the formula, $A^9$-$A^{11}$, which may be identical or different, each represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group. Each of $A^9$-$A^{11}$ preferably represents a hydrogen atom, a halogen atom, a non substituted $C_{1-10}$ alkyl group, a non substituted $C_{2-10}$ alkenyl group, a non substituted $C_{2-10}$ alkynyl group, or a non substituted $C_{1-10}$ alkoxy group. More preferred $A^9$-$A^{11}$ is a methyl group or an ethyl group.

A preferred embodiment of the first aspect of this resin medical product invention is that the phosphorylcholine derivative is a co-polymer (Co-polymer 2) of phosphorylcholine derivative and hydrophilic monomer, the co-polymer is represented by formula (A2).

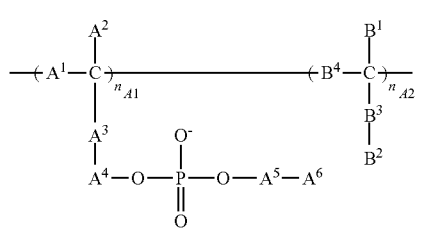

(A2)

$n_{A1}$ and $n_{A2}$ represent the number from 20 to 2000 that may be the same or different. The $n_{A1}$ and $n_{A2}$, as well as the molecular weight of Co-polymer 2 may be the same or similar to those of chemical compounds represented by the formula (I) or (II). $A^1$, $A^2$, $A^3$, $A^4$, $A^5$, and $A^6$ represent the same as explained the above.

$B^1$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group.

$B^2$ represents an optionally substituted $C_{1-10}$ alkyl group, an optionally substituted $C_{2-10}$ alkenyl group, an optionally substituted $C_{2-10}$ alkynyl group, an optionally substituted $C_{1-10}$ alkoxy group, or a group that is represented as (—N($B^7B^8$)).

$B^3$ represents any one of the group represented in formula (A5), an optionally substituted $C_{1-8}$ alkylene group, an optionally substituted $C_{2-7}$ alkenylene group, an optionally substituted $C_{2-7}$ alkynylene group, or a group that is represented as (—COO—$B^9$—).

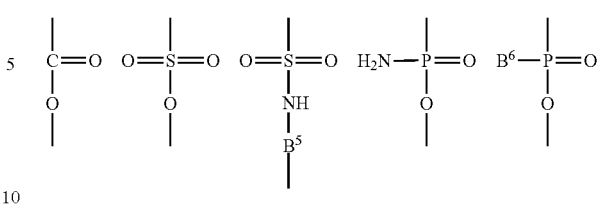

(A5)

$B^4$ represents a single bond, an optionally substituted $C_{1-10}$ alkylene group, an optionally substituted $C_{2-10}$ alkenylene group.

$B^5$ represents a single bond, an optionally substituted $C_{1-10}$ alkylene group, an optionally substituted $C_{2-10}$ alkenylene group. $B^6$ represents a hydrogen atom, a halogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group.

$B^7$ and $B^8$, which may be identical or different, each represents a hydrogen atom, an optionally substituted $C_{1-10}$ alkyl group, an optionally substituted $C_{2-10}$ alkenyl group, an optionally substituted $C_{2-10}$ alkynyl group, or an optionally substituted $C_{1-10}$ alkoxy group. $B^9$ represents a $C_{1-8}$ alkylene group, a $C_{2-7}$ alkenylene group, or a $C_{2-7}$ alkynylene group.

Examples of the monomer unit that composes the co-polymer with the phosphorylcholine derivative are a hydrophilic monomer and a base monomer (an alkali monomer). The followings are the preferred examples of the embodiment that has a hydrophilic monomer as the monomer unit with the phosphorylcholine derivative.

$B^1$ represents a hydrogen atom, a halogen atom, a $C_{1-10}$ alkyl group, a $C_{2-10}$ alkenyl group, a $C_{2-10}$ alkynyl group, or a $C_{1-10}$ alkoxy group. $B^1$ preferably represents a $C_{1-5}$ alkyl group, more preferably represents a methyl group or an ethyl group.

$B^2$ represents a $C_{1-10}$ alkyl group, a $C_{2-10}$ alkenyl group, a $C_{2-10}$ alkynyl group, or a $C_{1-10}$ alkoxy group. $B^2$ preferably represents a $C_{2-7}$ alkyl group, more preferably represents a $C_{3-5}$ alkyl group.

$B^3$ represents any one of the group represented in formula (A5). $B^3$ preferably represents a group represented by the formula (—CO$_2$—).

$B^4$ represents a single bond, a $C_{1-10}$ alkylene group, a $C_{2-10}$ alkenylene group. $B^4$ preferably represents a $C_{1-5}$ alkylene group, more preferably represents a $C_{1-2}$ alkylene group.

$B^5$ represents a single bond, a $C_{1-10}$ alkylene group, a $C_{2-10}$ alkenylene group. $B^5$ preferably represents a single bond or a $C_{1-5}$ alkylene group, more preferably represents a methylene group.

$B^6$ represents a hydrogen atom, a halogen atom, a $C_{1-10}$ alkyl group, a $C_{2-10}$ alkenyl group, a $C_{2-10}$ alkynyl group, or a $C_{1-10}$ alkoxy group. $B^6$ preferably represents a hydrogen atom or a $C_{1-5}$ alkyl group, more preferably represents a methyl group.

The followings are the preferred examples of the embodiment that has a base monomer as the monomer unit with the phosphorylcholine derivative.

$B^1$ represents a hydrogen atom, a halogen atom, a $C_{1-10}$ alkyl group, a $C_{2-10}$ alkenyl group, a $C_{2-10}$ alkynyl group, or a $C_{1-10}$ alkoxy group. $B^1$ preferably represents a $C_{1-5}$ alkyl group, more preferably a methyl group or an ethyl group.

$B^2$ represents a group that is represented as (—N($B^7B^8$)).

$B^3$ represents a $C_{1-8}$ alkylene group, a $C_{2-7}$ alkenylene group, a $C_{2-7}$ alkynylene group, or a group that is represented as (—COO—B⁹—). B³ preferably represents a $C_{1-8}$ alkylene group, more preferably represents a $C_{2-5}$ alkylene group.

B⁴ represents a single bond, a $C_{1-10}$ alkylene group, or a $C_{2-10}$ alkenylene group. B⁴ preferably represents a $C_{1-5}$ alkylene group, more preferably represents $C_{1-2}$ alkylene group.

B⁷ and B⁸, which may be identical or different, each represents a hydrogen atom, a $C_{1-10}$ alkyl group, a $C_{2-10}$ alkenyl group, a $C_{2-10}$ alkynyl group, or a $C_{1-10}$ alkoxy group. Each of B⁷ and B⁸ preferably represents a hydrogen atom or a $C_{1-5}$ alkyl group, more preferably represents a hydrogen atom or a $C_{1-2}$ alkyl group.

B⁹ represents a $C_{1-8}$ alkylene group. B⁹ preferably represents a $C_{1-5}$ alkylene group, more preferably represents $C_{1-2}$ alkylene group.

The present invention also provides the use of polymer 1 or polymer 2 in the manufacture of plastic products for medical use. In addition, the present invention also provides a method for preventing elution of the polymeric plasticizer using polymer 1 or 2. The present invention provides a method for preventing elution of the plasticizer that includes the step of forming a coating layer that comprises a polymer 1 or 2. The present invention further provides a method for producing a resin product for medical use that includes the step of forming a coating layer that comprises a polymer 1 or 2. A method of forming a coating layer is similar to the method described below to prepare a coating layer.

The present invention further provides the use of polymer 1 or polymer 2 to prevent a disease that is induced by eluting the resin plasticizer contained in the medical resin products. The example of disease that is caused by the elution of the plasticizer that is inflammation. The present invention also provides a method for preventing disease that is caused by the elution of the plasticizer that is inflammation by means of using the polymer 1 or polymer 2.

As used herein, the term "a single bond" is a bonding format that does not have a carbon atom. For example, $CH_2$-(single bond)-$CH_2$ means an ethane molecule. Examples of the halogen atom are fluorine, chlorine, bromine and iodine.

The term "$C_{m-n}$" means the number of carbon atoms is from m to n.

The examples of substitute groups in an optionally substituted $C_{1-10}$ alkyl group, an optionally substituted $C_{2-10}$ alkenyl group, an optionally substituted $C_{2-10}$ alkynyl group, an optionally substituted $C_{2-10}$ alkenylene group, an optionally substituted $C_{2-10}$ alkynylene group, and an optionally substituted $C_{1-10}$ alkoxy group, are a halogen atom, a hydroxyl group, a nitro group, and a cyano group. The number of the substitute groups is not limited to 0, 1 or several (2 to 5). Further, when one molecule has several substitute groups, they may be the same or different.

The $C_{1-10}$ alkyl group means a straight-chain or a branched chain alkyl group that has one to ten carbon atoms. Examples of the straight-chain alkyl group are a methyl group, an ethyl group, a n-propyl group, a iso-propyl group, a n-butyl group, a iso-butyl group, a sec-butyl group, a tert-butyl group, a n-pentyl group, a 1,1-dimethyl propyl group, a 1,2-dimethyl propyl group, a 2,2-dimethylpropyl group, a 1-ethylpropyl group, a 2-ethylpropyl group, a hexyl group, a 1-methyl-2-ethylpropyl group, a 1,1,2-trimethylpropyl group, a 1-propylpropyl group, a 1-methylbuthyl group, a 1,2-dimethylbutyl group, a 2,2-dimethylbutyl group, a 1,3-dimethylbutyl group, a 2,3-dimethylbutyl group, a 2-ethylbutyl group, a 2-methylpentyl group, and a 3-methylpentyl group.

The $C_{2-10}$ alkenyl group means a straight-chain or a branched alkynyl group that has two to ten carbon atoms. Examples of $C_{2-10}$ alkenyl group are a vinyl group, allyl group, a 1-propenyl group, a 2-propenyl group, an iso-propenyl group, a 2-methyl-1-propenyl group, a 3-methyl-1-propenyl group, a 2-methyl-2-propenyl group, a 3-methyl-2-propenyl group, a 1-butenyl group, a 2-butenyl group, a 3-butenyl group, a 1-pentenyl group, a 1-hexenyl group, a 1,3-hexanediol dicyclopentadienyl group, and a 1,6-hexanediol dienyl group.

The $C_{2-10}$ alkynyl group means a straight-chain or a branched alkynyl group that has two to ten carbon atoms. Examples of $C_{2-10}$ alkynyl group are an ethynyl group, a 1-propynyl group, a 2-propynyl group, a 1-butynyl group, a 2-butynyl group, a 3-butynyl group, a 3-methyl-1-propynyl group, a 1-ethynyl-2-propynyl group, a 2-methyl-3-propynyl group, a 1-pentynyl group, a 1-hexynyl group, a 1,3-hexane dinyl group, and a 1,6-hexane dinyl group.

The $C_{1-10}$ alkylene group means a divalent group that is formed in a manner that one more hydrogen atom is removed from a $C_{1-10}$ alkyl group. Examples of $C_{1-10}$ alkylene group are a methylene group, an ethylene group, a methyl ethylene group, a propylene group, an ethyl-ethylene group, a 1,1-dimethyl-ethylene group, a 1,2-di-methyl-ethylene group, a tri-methylene group, a 1-methyl-tri-methylene group, a 1-ethyl tri-methylene group, a 2-methyl tri-methylene group, a 1,1-di-methyl-tri-methylene group, a tetra-methylene group, a pentamethylene group, and a hexa-methylene group.

The $C_{2-10}$ alkenylene group means a divalent group that is formed in a manner that one more hydrogen atom is removed from a $C_{2-10}$ alkenyl group. Examples of $C_{2-10}$ alkenylene group are a vinylene group, a propenylene group, a butenylene group, a pentenylene group, and a hexenylene group.

The $C_{2-7}$ alkynylene group means a divalent group that is formed in a manner that one more hydrogen atom is removed from a $C_{2-7}$ alkynyl group. Examples of alkynylene group are an ethynylene group, a propynylene group, a buthylene group, a pentenylene group, and a hexenylene group.

The $C_{1-10}$ alkoxy group means a group that is formed in a manner that a hydroxyl group is bonded to a $C_{1-10}$ alkyl group. Examples of $C_{1-10}$ alkoxy group are a methoxy group, an ethoxy group, a n-propoxy group, an iso-propoxy group, a sec-propoxy group, a n-butoxy group, an iso-butoxy group, a sec-butoxy group, a tert-butoxy group, a n-pentyloxy group, an iso-pentyloxy group, a sec-pentyloxy group, a n-hexoxy group, an iso-hexoxy group, a 1,1-dimethyl-propyloxy group, a 1,2-dimethyl-propoxy group, a 2,2-dimethyl-propyloxy group, a 2-ethyl-propoxy group, a 1-methyl-2-ethyl-propoxy group, a 1-ethyl-2-methyl-propoxy group, a 1,1,2-trimethyl-propoxy group, a 1,1,2-tri-propoxy methyl group, a 1,1-dimethyl-butoxy group, a 1,2-dimethyl-butoxy group, a 2,2-dimethyl-butoxy group, a 2,3-dimethyl-butyloxy group, a 1,3-dimethyl-butyloxy group, a 2-ethylbutoxy group, a 1,3-dimethyl-butoxy group, a 2-methylpentoxy group, a 3-methylpentoxy group, and a hexyloxy group.

The second aspect of this invention relates to a respiratory support tube. The respiratory support tube has a coating layer. The coating layer 2 has polymer that has a 2-methacryloyloxy ethyl phosphorylcholine (MPC) (the following formula (III)) (the "MPC polymer").

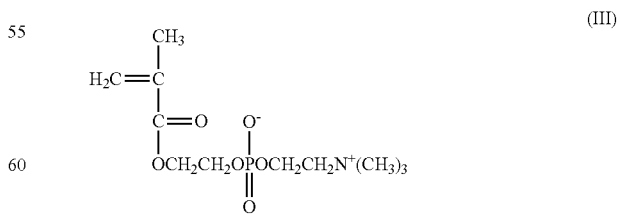

(III)

In the present invention, the surface of the respiratory support tube means the surface of the tube at which the tube contacts with living tissue. The surface at which the tube contacts with living tissue means the surface that contacts with the living tissue when the tube is attached, removed or in use. The surface at which the tube contacts with living tissue may be a part or whole of the outside surface of the respiratory support tube.

Examples of the respiratory support tube are an endotracheal tube, a bronchial tube, a tracheostomy tube, a laryngeal tracheal tube, and an esophagus tube. It is preferred that the respiratory support tube has a cuff attached to the respiratory support tube. The respiratory support tube may be a cuff less tube. The respiratory support tube for new born babies and for infants usually does not have a cuff. The reason of the shape is that the tracheas of them are not horseshoe round but a cylindrical shape.

Example of the respiratory support tube of the present invention is a laryngeal mask.

An example of the respiratory support tube of the present invention is the endotracheal tube that has a cuff attached to the tube. The endotracheal tube that has a cuff has a tube body and a cuff which is attached to the vicinity of the tip end portion of the tube and surrounds with seal to a part of the outside surface of the tube. The cuff may be composed of a thin film and has a spherical shape or elliptical shape. The endotracheal tube that has a cuff may have a tube that is used to expand and shrink the cuff so as to expand and shrink the cuff in a patient's trachea when the endotracheal tube is inserted into the patient's trachea. The tube that is used to expand and shrink the cuff has a pilot balloon and a small diameter tube that connects with the pilot balloon. The pilot balloon connects with the small diameter tube at the tip end of the small diameter tube. The other tip end of the small diameter tube may be connected to the tube body. The connect part that connects the small diameter tube and the tube body may be configured to be between the cuff part and the part of the tube body that does not has the cuff. The length of the tube body of the present invention is, for example, 20 to 50 cm and the thickness of the tube body is, for example, 0.5 to 5 mm. The inner diameter of the tube body, which is count without considering the part of cuff, is for example, 4 to 12 mm. The inner diameter of the cuff when it is expanded is, for example, 1 to 5 cm. The thickness of the thin film that composes the cuff is, for example, 0.01 to 1 mm. The volume of the cuff is, for example, 10 to 100 mL. However, the volume may be designed to less than 10 mL or more than 100 mL based on the required usage. Because the cuff part may be expanded, it is preferred that the material of the cuff has a trait of expansion and shrinkage. As shown in the FIG. 2, the tube may have a proportion which is directed to inner direction of the tube from the inner wall of the tube. The shape of the proportion may be spiral along with the direction of the longitudinal direction of the tube. As explained above, it is possible to arrange the shape of the tube with considering the age of the patient, the gender of the patient and usage of the tube.

The respiratory support tube of the present invention may be made of, for example, polyolefin elastomers that comprise polyethylene, polypropylene, or ethylene-propylene copolymer; thermoplastic resins that compose polyvinyl chloride, ethylene-vinyl acetate copolymer, polyamide elastomer or polyurethane; silicone rubber; or latex rubber. During the insertion of the respiratory support tube, the shape of surroundings of the tube in human body continuously changes. Thus if the respiratory support tube were so hard it could not adjust the change of shape and thus it would press organs or cells of the patient. In such a case, the patient will feel pain when the respiratory support tube is inserted. On the other hand, if the respiratory support tube is softened, it can change shape adjusting shape change of inner shape of the human body and thus it would not give damages to the patient. In this aspect, it is preferred that the respiratory support tube of the present invention may be made of thermoplastic resin such as phthalates, polyvinyl chloride, ethylene-vinyl acetate copolymer, polyamide elastomer, or polyurethane, more preferably made of polyvinyl chloride. Polyvinyl chloride product is hard when it is outside the human body but it softened when it is inserted into the human body because of the human temperature and thus it can prevent pain. However, a respiratory support tube made of such a material is tightly adhesive to human tissues. Thus when such a respiratory support tube contacts to human tissues in using the tube, it removes human cells and cause damages to human cells when the tube is detached. Therefore, as shown in the working examples, by coating a tube made by thermoplastic resin with MPC polymer has a meritorious effect that it does not remove human cells keeping the characteristic that it softens by human temperature. The respiratory support tube of the present invention may be made by already known method and it is possible to use commercially available tube as the respiratory support tube.

As explained above, it is preferred to use plastic material, plasticizer, as the ingredient of the respiratory support tube because the present invention can prevent pain of the patient. However, plasticizer in the respiratory support tube may be transferred to human tissues through the part the respiratory support tube attaches to human tissues. If the plasticizer were transferred to human tissues, human cells suffer damages and cause pain to the patient. However, in case of the respiratory support tube of the present invention, there is a layer that comprises MPC between the respiratory support tube and human tissues. The layer can prevent plasticizer from being transferred to human tissues. Thus the respiratory support tube of the present invention can prevent inflammation caused by adhesion of the respiratory support tube and human tissues.

The coating layer of the respiratory support tube in the present invention means a layer that is formed by contacting MPC polymer with the surface of the respiratory support tube. Ingredients of the coating layer does not limited to MPC. The coating layer may comprise, for example, solvent which is used in a step of coating within manufacturing steps of the respiratory support tube. Containing ratio of MPC in the coating layer may be, when total amount of the ingredients in the coating layer is set to be 100 weight parts, 60 to 100 weight parts, and is preferably 90 to 99 weight parts and is more preferably 80 to 95 weight parts. Example of the thickness of the coating layer of the respiratory support tube is $1 \times 100$ to $1 \times 10^4$ micro meters, and is preferably $5 \times 10^0$ to $1 \times 10^3$ micro meters, and is more preferably $1 \times 10^1$ to $5 \times 10^2$ micro meters. The thickness of the coating layer may be defined as the largest distance from the outer surface of the respiratory support tube and the outer surface of the coating layer. The outer surface of the coating layer is surface that is not attached to the outer surface of the respiratory support tube. It is preferred that the thickness of the coating layer is uniform but it may not be uniform. It is preferred that the thickness of the part that attaches to human tissues is larger than that of the part that does not attaches to human tissues, when the thickness of the coating layer is not uniform. The thickness of the coating layer may be measured by a well known meter that can measure thickness of membrane.

An example of MPC polymer is shown in the following formula (IV).

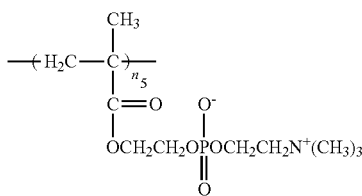

(IV)

Wherein $n_5$ is an integer of 50 to 2000; preferably it is 100 to 1,500; more preferably it is 200 to 1,000; still more preferably it is 350 to 800. Thus, an average number molecular weight of the MPC polymer is, for example, $1\times10^4$ to $5\times10^5$; preferably it is $3\times10^4$ to $4\times10^5$; more preferably it is $5\times10^4$ to $3\times10^5$; still more preferably $1\times10^5$ to $3\times10^5$ is more preferred.

The MPC polymer may be prepared using known methods or commercially available MPC may be used. The following is an example of the method for manufacturing MPC polymer. First, 2-distearate bromoethyl phosphoryl chloride, 2-hydroxyethyl distearate phosphoryl chloride and 2-hydroxyethyl methacrylate are reacted to obtain 2-methacryloyloxy ethyl-2'-bromoethyl phosphoric acid. Then it is reacted with trimethylamine in a methanol solution (Japanese Patent Publication No. H05-070321 A). Then, by making MPC react each other is a solvent with the presence of a polymerization initiator to obtain MPC polymers. The solvent may dissolve the MPC. The solvent into which MPC dissolve is, for example, water, methanol, ethanol, propanol, t-butanol, benzene, toluene, dimethylformamide, tetrahydrofuran, chloroform, or mixtures of these solvents. The polymerization initiator may be already known radical initiator and examples of the polymerization initiator are azo compounds such as 2,2'-azobisisobutyronitrile (AIBN) and fatty acid azo nitrile; organic peroxides such as benzoyl peroxide, lauroyl peroxide, and potassium persulfate. A skilled person may select suitable solvent and polymerization initiator to manufacture MPC polymer.

As shown in the above formula (IV), MPC polymer of the present invention has a polar group with a phospholipid (phosphorylcholine group ($-O-PO_2-O-CH_2CH_2-N^+(CH_3)_3$), which constitutes bio membranes. The phosphorylcholine group is included in the cell membrane (membrane double lipid) contained. Therefore, the respiratory support tube of the present invention has an excellent biocompatibility because it has coating layer having MPC polymer. Thus the respiratory support tube of the present invention is suitable as a tube which is used into human body.

The MPC polymer of the present invention may comprise copolymers that have an MPC monomer and a monomer selected from a basic (alkali) monomer and a hydrophobic monomer (the following formula (V)) or that have a MPC monomer, a basic monomer and a hydrophobic monomer (the following formula (VI)). A skilled person can select a basic monomer and a hydrophobic monomer from already known compounds because they can polymerize with MPC.

(V)

In the formula, X represents a basic monomer or a hydrophobic monomer. The $n_6$ and $n_7$, which may be identical or different, represent an integer of 20 to 1500.

(VI)

In the formula, Y and Z represent a basic monomer or a hydrophobic monomer. The $n_8$, $n_9$ and $n_{10}$, which may be identical or different, represent an integer of 20 to 1500.

The basic monomer is explained below.
An example of the basic monomer in the present invention is the compound that has the following formula (VII).

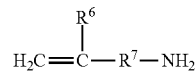

(VII)

In the formula (VII), $R^6$ represents H or a $C_{1-3}$ alkyl group, and preferably represents H or a methyl group. $R^7$ represents a $C_{1-8}$ alkylene group, a $C_{2-7}$ alkenylene group, a $C_{2-7}$ alkynylene group, and preferably represents a $C_{1-5}$ alkylene group, and more preferably represents a $C_{1-3}$ alkylene group. $R^7$ may be a straight chain or a branched chain. It is preferred for $R^7$ to be a straight chain. The compounds represented by the above formula (VII) are already known and thus a skilled person can manufacture them.

The copolymer that is obtained by reacting MPC monomer and a basic monomer (a basic copolymer is explained hereafter)). This copolymer is shown in the following chemical formula (II).

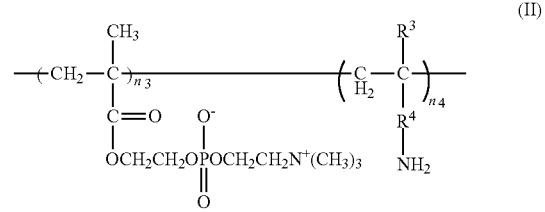

(II)

In chemical formula (II), $R^3$ represents H or a $C_{1-3}$ alkyl group. $R^4$ represents a $C_{1-8}$ alkylene group, a $C_{2-7}$ alkenylene group, a $C_{2-7}$ alkynyl group having 2 to 7 or a group represented by $-COO-R^5-$, wherein $R^5$ represents a $C_{1-8}$ alkylene group, a $C_{2-7}$ alkenylene group or a $C_{2-7}$ alkynyl group. $R^4$ and $R^5$ may be a straight chain or a branched chain. It is preferred for $R^4$ and $R^5$ to be a straight chain. The $n_3$ and $n_4$, which may be identical or different, represent an integer of 20 to 1500, preferably represent 100 to 1000, and more preferably represent 200 to 800. The above basic copolymer may be manufactured based on already known method or commercially available one may be used.

The example of the number average molecular weight of the basic copolymer of the present invention which is contained in the coating layer is $1\times10^4$ to $5\times10^5$. If the number average molecular weight were so little or so large, then it is difficult to obtain a flat coating layer; namely it is difficult to manufacture a coating layer with desired thickness. Thus preferred example of the number average molecular weight of the basic copolymer is $5\times10^4$ to $3\times10^5$ and more preferably is $1\times10^5$ to $3\times10^5$. The example of the mole ratio between MPC monomer and basic monomer of the basic copolymer contained in the coating layer of the present invention ($n_3:n_4$) is 1:10 to 10:1. When the ratio of the MPC monomer in the basic copolymer becomes higher, the adhesiveness between the respiratory support tube and the basic copolymer decreases. Thus the preferred example of the mole ratio between MPC monomer and basic monomer in the coating layer ($n_3:n_4$) is 1:5 to 5:1 and is preferably 1:3 to 3:1.

The basic group of the basic copolymer reacts with a carboxyl group or a glycosyl group that exists on the surface of the respiratory support tube and makes a bonding by means of an ion bonding when the coating layer of the present invention has basic copolymers. Thus in such a case the coating layer has two layer membrane structure such as cell membranes. This coating layer of two layer membrane has low adhesiveness to cells or proteins in a living body. Thus the respiratory support tube which has the above mentioned coating layer has less influence on patient's organs and thus it can prevent inflammation after using a respiratory support tube. Therefore, the respiratory support tube that has basic copolymers is preferably used into a body of living things.

The hydrophobic monomer is explained hereafter.
The examples of the hydrophobic monomers of the invention have the following formula (VIII).

(VIII)

In formula (VIII) $R^8$ represents H or a $C_{1-3}$ alkyl group, and preferably represents H or a methyl group. $R^9$ represents a $C_{4-15}$ alkyl group, a $C_{4-15}$ alkenyl group, or a $C_{4-15}$ alkynyl group, preferably represents a $C_{4-10}$ alkyl group, a $C_{5-10}$ alkenyl group, or a $C_{5-10}$ alkynyl group and more preferably represents a $C_{4-8}$ alkyl group. $R^9$ may be a straight chain or a branched chain. The methacrylic acid esters represented by the formula (VIII) are already known and a skilled person can manufacture them.

Copolymer obtained by reaction of the MPC monomer and hydrophobic monomer (hereinafter called "hydrophobic copolymer") is explained bellow. The hydrophobic copolymers are represented by the formula (I).
The coating layer of the respiratory support tube is co-polymer of 2-methacryloyloxy ethyl phosphorylcholine of formula and hydrophobic monomer, the co-polymer is represented in formula (I):

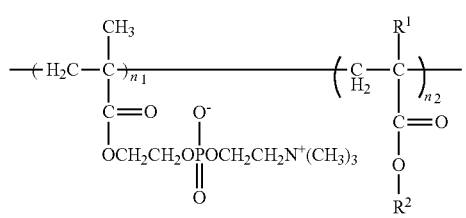

(I)

In the formula (I), $R^1$ represents H, or a $C_{1-3}$ alkyl group, preferably represents H or a methyl group. $R^2$ represents a $C_{4-15}$ alkyl group, a $C_{4-15}$ alkenyl group, or a $C_{4-15}$ alkynyl group and preferably represents a $C_{4-8}$ alkyl group. $R^2$ may be a straight chain or a branched chain. The $n_1$ and $n_2$ are the same or different, each represents an integer from 20 to 1500, preferably represents 100 to 1000, more preferably represents 150 to 800. The above hydrophobic copolymer is already known and a skilled person can manufacture them.

The example of the number average molecular weight of the hydrophobic copolymer of the present invention which is contained in the coating layer is $1 \times 10^4$ to $5 \times 10^5$, preferably is $5 \times 10^4$ to $3 \times 10^5$ and more preferably is $1 \times 10^5$ to $3 \times 10^5$. The example of the mole ratio between MPC monomer and hydrophobic monomer of the hydrophobic copolymer contained in the coating layer of the present invention ($n_1:n_2$) is 1:10 to 10:1. When the ratio of the MPC monomer in the hydrophobic copolymer becomes higher, the adhesiveness between the respiratory support tube and the basic copolymer decreases. Thus the preferred example of the mole ratio between MPC monomer and basic monomer in the coating layer ($n_1:n_2$) is 1:5 to 5:1 and is preferably 1:3 to 3:1.

In the present invention, a coating layer including a hydrophobic copolymer is such that a hydrophobic group in a basic copolymer binds, via a hydrophobic bonding, to a hydrophobic group present on the surface of a breathing assistance tube. Due to this, the resultant coating layer has a dual membrane form such as a cell membrane. This coating layer has low adhesion to cells and proteins in vivo. Therefore, a breathing assistance tube having such a coating layer has less influence on the living tissues of patients, and thus can alleviate the possibility of the development of inflammation after use of the tube. Accordingly, the breathing assistance tube having a coating layer including a hydrophobic copolymer can suitably be used in vivo.

When conventional breathing assistance tubes were removed out of a living body, cells in the living tissues were exfoliated due to high adhesion between the surface of the breathing assistance tube and the cell surfaces of the living tissues. Therefore, such conventional breathing assistance tubes involved the problem that inflammatory reactions occur because of the exfoliation of cells. However, the breathing assistance tube of the present invention can prevent the event that cells of living tissues adhere to the breathing assistance tube and then are exfoliated at the time of attachment or detachment thereof, as will be described in the Examples below. Therefore, the breathing assistance tube of the present invention can prevent damage on living tissues. As a result, the breathing assistance tube of the present invention can avoid inflammatory reactions due to the use of the tube. Further, the breathing assistance tube of the present invention does not damage living tissues at the time of attachment or detachment thereof, and thus can prevent the event that cilia in the trachea are lost, as will be described in the following Examples. Therefore, the function of the cilia to discharge sputum would not be deteriorated, and thus the breathing assistance tube of the present invention can avoid pneumonia which would be caused by sputum entering the lung. In addition, the breathing assistance tube of the present invention does not cause any friction even when the tube and living tissues are rubbed against each other during the use thereof or at the time of attachment or detachment thereof, as will be indicated in the following Examples. This prevents the event that the living tissues which are in contact with the breathing assistance tube are damaged. Accordingly, avoided is granulation or cicatrization due to the patients' own healing power after tissue damaging. Thus, the breathing assistance tube of the present invention can avoid diseases including respiration disorder caused by granulation or cicatrization.

A further preferred aspect of the present invention is a breathing assistance tube having a coating layer including trehalose. Trehalose includes three isomers referred to as α, α substance, α,β substance and β, β substance which are different in binding manner. In the present invention, so long as one or more of these isomers are included in an effective amount as a whole, any process for the preparation thereof, purity and nature may be employed. The amount of trehalose to be contained in the coating layer is 0.1 part to 40 parts by weight, preferably 0.5 part to 20 parts by weight, and more preferably 1 part to 10 parts by weight when the total amount of an MPC polymer, a hydrophobic copolymer or a basic copolymer and trehalose in the coating layer is defined as 100 parts by weight in the present invention. The breathing assistance tube has further improved biocompatibility due to the incorporation of trehalose into the coating layer. In addition, the incorporation of trehalose into the coating layer enhances the binding of the MPC polymer, hydrophobic copolymer or basic copolymer to the breathing assistance tube.

Next, a process for making the coating layer of the breathing assistance tube will be explained.

A process for making the coating layer of the breathing assistance tube according to the present invention includes the coating step of applying a coating liquid including a coating agent to a breathing assistance tube. In the meantime, the coating agent includes any one, or two or more, of an MPC polymer, a hydrophobic copolymer and a basic copolymer in the present invention. The coating agent may further include trehalose in the present invention. A known method such as a dipping, brushing, spraying or spin-coating method may be used as the method for coating a breathing assistance tube with the coating liquid in this process.

The amount of the MPC polymer, hydrophobic copolymer or basic copolymer in the coating liquid is 0.01 part to 50 parts by weight when the total weight of the coating liquid is defined as 100 parts by weight. Too large an amount of the polymer or copolymer in the coating liquid increases the viscosity of the coating liquid. Therefore, the thickness of the coating layer of the breathing assistance tube becomes non-uniform easily. On the other hand, too small an amount of the polymer or copolymer in the coating liquid requires an increased frequency of coating in order to obtain a desired coating layer, which is troublesome. Hence, the amount of the polymer or copolymer in the coating liquid is preferably 0.1 part to 30 parts by weight, and more preferably 0.5 part to 10 parts by weight. In the present invention, when trehalose is further incorporated into the coating liquid, the amount thereof is 0.1 part to 20 parts by weight, preferably 0.5 part to 15 parts by weight, and more preferably 1 part to 10 parts by weight when the total weight of the coating liquid is defined as 100 parts by weight.

The coating liquid used in the coating step of the present invention can be used in the form of a solution or a slurry. To make the thickness of the coating layer uniform, the coating liquid is preferably used in the form of a solution (coating solution). The coating solution may be prepared by dissolving a coating agent in a solvent. Such a solvent includes, for example, water; various buffers such as an acetate buffer, a phosphate buffer, a tris-hydrochloride buffer, a carbonate buffer and a Good's buffer; and a solution containing a single one, or a mixture of two or more, of various organic solvents such as methanol, ethanol, propanol, ethylene glycol, glycerine, dimethyl sulfoxide and dimethylformamide. Those skilled in the art can appropriately select and use the solvent depending on the material for the breathing assistance tube or the properties of the coating agent.

The coating step of the present invention will now be explained in detail based on the dipping method. The dipping method includes, in the coating step of the present invention, the dipping step of dipping the breathing assistance tube in the coating solution and the drying step of removing the thus-dipped breathing assistance tube from the coating solution and then drying the tube. In the present invention, the temperature of the coating liquid during the dipping step is 5 to 100° C. Too high a coating liquid temperature lowers the viscosity of the coating liquid so that the coating liquid is hard to deposit onto the breathing assistance tube. On the other hand, too low a coating liquid temperature increases the viscosity of the coating liquid, thereby making it difficult to obtain a uniform thickness of the coating layer of the breathing assistance tube. Therefore, the coating liquid temperature is preferably 10 to 50° C., and more preferably 15 to 30° C. The dipping time is 5 seconds to 5 hours. In the present invention, the temperature during the drying step is not especially limited, and is 5 to 100° C. The drying step may be carried out in a windless state or at a wind rate of 0.1 to 10 m/s. In addition, both the dipping step and drying step may be carried out either at ordinary pressure or under pressure in the present invention. Those skilled in the art can appropriately determine the pressure depending on the material for the breathing assistance tube to be used and the properties of the coating liquid.

In the present invention, coating is carried out once or more than once. When coating is carried out more than once, the frequency of coating is twice to twenty times, but may also be 21 times or more. Coating may be carried out more than once either by the same method or different methods. In the present invention, the thickness of the coating layer formed by coating is $1 \times 10^0$ to $1 \times 10^4$ μm, preferably $5 \times 10^0$ to $1 \times 10^3$ μm, and more preferably $1 \times 10^1$ to $5 \times 10^2$ μm. Those skilled in the art can appropriately control the thickness of the coating layer depending on the intended use purpose by changing the frequency of coating or the like. Those skilled in the art can measure the thickness of the coating layer by means of a known film thickness meter.

In the present invention, the place of the breathing assistance tube to be covered with the coating layer is the entire or part of a site in contact with living tissues during the use of the breathing assistance tube or at the time of attachment or detachment thereof. Those skilled in the art can understand a site at which the breathing assistance tube and living tissues depending on the intended use of the breathing assistance tube. In the meantime, the breathing assistance tube may be coated either on the entire outer surface thereof or only on a place in contact with the living tissues in the present invention. For example, when a cuffed breathing assistance tube is coated, the tube may be coated either on the entire outer surface thereof or only on a cuff portion in contact with living tissues. Coating of the breathing assistance tube may also be carried out on the entire inner cavity wall thereof in addition to the entire outer surface thereof. Coating of the outer surface and inner cavity wall of the breathing assistance tube inhibits the deposition of a biofilm including an extracellular polysaccharide onto the breathing assistance tube. This biofilm is produced from bacteria on the surface of the breathing assistance tube to play a role in depositing bacteria on a growth place or protecting bacteria from exogenous attacks. Thus, the breathing assistance tube coated not only on its outer surface, but also on its inner cavity wall can prevent the growth of bacteria (biofilm formation) on the breathing assistance tube in patients who require respiratory management over a long term. This can, therefore, avoid the event that patients suffer from bacterial ventilator-associated pneumonia (VAP).

The breathing assistance tube of the present invention can be inserted from the mouth, nasal cavity or incision opening for use in order to secure breathing. The breathing assistance tube of the present invention coated with an MPC polymer can prevent damage to living tissues during the use thereof or at the time of attachment or detachment thereof, as described above, and, as a result, can avoid inflammatory reactions during the use thereof. Further, the breathing assistance tube of the present invention can alleviate the risk of development of postoperative pneumonia. Furthermore, the breathing assistance tube of the present invention can prevent granulation or cicatrisation. Additionally, the breathing assistance tube of the present invention can prevent the event of the transfer, to living tissues, of a plasticizer as a material for producing the breathing assistance tube. Further, the breathing assistance tube of the present invention can prevent the event of the formation of a biofilm within the tube during use. Thus, the breathing assistance tube of the present invention can avoid respiratory complications (for example, postoperative pneumonia, postoperative atelectasis and respiratory failure) which can be caused by the short-term use of the tube in vivo as well as ventilator-associated pneumonia which can be caused by the long-term use thereof in vivo.

Hereinafter, the Examples of the present invention will be explained. However, the present invention is not limited thereto, and those skilled in the art can appropriately add modifications thereto. Especially, the coating layer of the present invention has hydrophilicity and hydrophobicity, and includes a polymer having a structure similar, to a certain extent, to that of MPC, and thus provides advantageous effects. Thus, the present invention is not limited to MPC or the like which will be explained below.

Example 1

A cuffed tracheal tube was used as a breathing assistance tube. The cuffed tracheal tube was coated with a coating solution, and then inserted into the canine trachea. Four to Five hours after the insertion, the cuffed tracheal tube was removed to investigate the amount of cells deposited onto the cuffed tracheal tube and the damage on the canine trachea. In the meantime, a copolymer (PMB 3070) including 2-methacryloyloxyethyl phosphorylcholine (MPC) and n-butyl methacrylate (manufactured by NOF Corporation) was used as the polymer of the present invention. 100% Ethanol was used as a solvent for PMB 3070. In the meantime, PMB 3070 is represented by the above Formula (I), wherein $R^1$ is a methyl group; $R^2$ is a butyl group; $n_1$ is about 300; and $n_2$ is about 700. The number average molecular weight of PMB 3070 is $2.5 \times 10^5$.

PMB 3070 was dissolved with 100% ethanol so that the amount thereof reached 0.5% or 5.0% by weight. The cuffed tracheal tube was coated by dipping in respective coating solutions. The following Table 1 shows coating conditions.

[Table 1]

TABLE 1

|  | Coating solution | Number of Coating |
|---|---|---|
| Control | None |  |
| 0.5% PMB3070 + treha × 2 | 0.5% PMB3070 + 10% Trehalose | 2 times |
| 0.5% PMB3070 × 2 | 0.5% PMB3070 | 2 times |
| 0.5% PMB3070 × 10 | 0.5% PMB3070 | 10 times |
| 5.0% PMB3070 × 1 | 5.0% PMB3070 | 1 time |

The amount of cells deposited onto the cuffed trachea tube detached from the canine trachea was investigated by hematoxylin staining. The results are shown in FIGS. 2 and 3. FIG. 2 shows a photograph alternative to the drawing of the cuffed tracheal tube stained with hematoxylin. It has been found that the cuffed trachea tube coated with 0.5% by weight of PMB 3070 solution ten times and the cuffed trachea tube coated with 5.0% by weight of PMB 3070 solution once were smaller than the control in terms of the amount of cells deposited onto the tube, as shown in FIG. 2.

FIG. 3 shows a photograph alternative to the drawing of the cuff part stained with hematoxylin. FIGS. 3A to 3C show photographs of the cuff part of the intratracheral tube without PMB 3070 coating (control). FIGS. 3D to 3F show photographs of the cuff part of the intratracheal tube coated with 0.5% by weight of PMB 3070 ten times (0.5% PMB 3070× 10). FIGS. 3G to 3I show photographs of the cuff part of the intratracheal tube coated with 5.0% by weight of PMB 3070 once (5.0% PMB 3070×1). FIGS. 3A, 3D and 3G show photographs of the cuff part at a magnification of 1. FIGS. 3B, 3F, and 3H show microphotographs of the cuff part taken at a magnification of 50. FIGS. 3C, 3F and 3I show microphotographs of the cuff part at a magnification of 400. As a result of this, the cells of the canine tracheal mucosa adhered to the control (FIGS. 3A to 3C), whereas the cuff part was weakly stained as a whole, but showed less adhesion of cells in the case of 0.5% PMB 3070×10 (FIGS. 3D to 3F). Further, in the case of 5.0% PMB 3070×1 (FIGS. 3G to 3I), the cuff part was not stained at all, or did not show cell adhesion. This has demonstrated that the coating of the intratracheal tube with PMB 3070 can efficiently prevent the exfoliation of cells on the surface of tissues onto which the intratracheal tube adhered.

Next, the portion stained with hematoxylin was binarized to calculate the proportion thereof with an image software. FIG. 4 shows the results. The vertical axis in FIG. 4A indicates the proportion of the stained region (%). The horizontal axis in FIG. 4B indicates the proportion of staining of the cuff part under other conditions when the proportion of the stained region of the control is defined as 100%. It has been found that 0.5% PMB 3070×10 provided an about 40% suppression of cell adhesion as compared with the control, as shown in FIGS. 4A and 4B. Further, it has been found that 5.0% PMB 3070×1 suppressed cell adhesion, by 99% or more, as compared with the control. It can be understood, also from this fact, that the coating of the intratracheal tube with PMB 3070 can efficiently prevent the exfoliation of cells on the surface of tissues onto which the intratracheal tube adhered.

Example 2

Four or five hours after the insertion of the cuffed tracheal tube into a canine, the canine was euthanized, and the cuffed tracheal tube was detached therefrom. After detachment of the tube, the canine was anatomized to observe the damage state of the trachea. FIG. 5 shows the results. FIG. 5A shows the canine trachea into which the cuffed tracheal tube not treated with PMB 3070 (control) was inserted. FIG. 5B shows the canine trachea into which the cuffed tracheal tube coated with 5.0% by weight of PMB 3070 once (5.0% PMB 3070×1) was inserted. As a result, the exfoliation of the tracheal mucosa was observed for the control (FIG. 5A). On the other hand, no exfoliation of the tracheal mucosa was observed for 5.0% PMB 3070×1 (FIG. 5B). Namely, it has been demonstrated that the coating of the intratracheal tube with PMB 3070 can prevent the exfoliation of cells at the insertion site.

Example 3

To a 35-mm dish, 100 μL of various coating liquids were applied (coated), and dried for 30 minutes at 40° C. After drying, the 35-mm dish was subjected to UV sterilization for 30 minutes in a clean bench. The sterilized 35-mm dish was wash with PBS (−) twice, and inoculated with L929 cells. After inoculation, the cells were cultured for 3 to 4 days. FIG. 6 shows the results. As the cell culture medium, a medium obtained by adding 10% FBS (fetal bovine serum) to a Dulbecco's modified Eagle medium (DMEM) was used. As the control, a 35-mm dish not coated with any coating liquid was used. A liquid obtained by dissolving PMB 3070 and trehalose in a 50% ethanol solution was used as the coating liquid. The concentrations of PMB 3070 and trehalose are indicated in the following Table 2.

TABLE 2

|  | PMB3070 | Trehalose |
|---|---|---|
| Control | None | None |
| 0.5% PMB3070 + 10% treha | 0.5% | 10% |
| 1.0% PMB3070 + 10% treha | 1.0% | 10% |
| 2.0% PMB3070 + 10% treha | 2.0% | 10% |
| 3.0% PMB3070 + 10% treha | 3.0% | 10% |
| 5.0% PMB3070 + 10% treha | 5.0% | 10% |

FIG. 6 shows a photograph alternative to the drawing showing that the coating of the dish with PMB 3070 and trehalose reduces cell adhesion. As a result, it has been demonstrated that the dish coated with PMB 3070 and trehalose reduces cell adhesion as compared with the control (FIG. 6A). It has also been demonstrated that, as the concentration of PMB 3070 in the coating liquid becomes higher, the cell adhesion is reduced. In view of the above, it can be said that the coating of the breathing assistance tube with a coating liquid including PMB 3070 and trehalose reduces the cell (tissue) adhesion onto the breathing assistance tube. Namely, it can be said to have demonstrated that the coating of the breathing assistance tube with PMB 3070 and trehalose can prevent the exfoliation of cells caused when the tube is detached.

Example 4

The suppression of the damage on the tracheal mucosa due to the tracheal tube coated with PMB 3070 was studied. The PMB 3070 polymer-coated (5.0% PMB 3070) cuff part of the cuffed tracheal tube and the untreated cuff part (control) thereof were each inserted into the canine trachea. Four to five hours after the insertion, the cuffed intratracheal tube was removed to collect the tracheal tissue. The collected portion which seemed to have been in contact with the cuff portion of the cuffed tracheal tube was photographed with a digital camera, and, thereafter, immersed in a sufficient amount of a 10% neutral formalin solution to fix the tissue for about 1 week. After the fixation, the tracheal tissue was sufficiently washed, and dipped in a bate for 3 to 4 hours for decalcification. After the decalcification, the tissue was dehydrated and defatted with an alcohol, and further dipped in xylene to remove the alcohol. After sufficient removal of the alcohol, the tissue was dipped and embedded in paraffin. Once the paraffin was solidified to make a block, thin sections were prepared by microtomy. The sections were stained with HE (hematoxylin-eosin) to observe them under a microscope (magnification: 100× and 200×). FIG. 7 shows the results.

FIGS. 7A and 7B and FIGS. 7C and 7D show photographs alternative to the drawings showing the canine tracheal tissue into which the control cuffed tracheal tube (no coating) and the cuffed tracheal tube coated with a liquid containing 5.0% PMB 3070, respectively, were inserted. For the canine tracheal tissue into which the control cuffed tracheal tube not coated with PMB 3070 was inserted (FIGS. 7A and 7B), a part of the epithelial layer is thin, and, additionally, an exfoliated portion is observed. Neutrophils such as macrophages are observed in places (blackish spherical cells), and inflammation has been induced. On the other hand, for the canine tracheal tissue into which the cuffed tracheal tube coated with PMB 3070 was inserted (FIGS. 7C and 7D), there is no exfoliation of epithelial cells, and a uniform mucosal layer is maintained. Further, it has been shown that no neutrotaxis is observed, and thus that tittle inflammation has occurred.

There is no exfoliation of epithelial cells in the canine tracheal tissue to/from which the PMB 3070-coated cuffed tracheal tube was attached/detached (FIGS. 7C and 7D). Thus, it has been demonstrated that the coating of the cuffed tracheal tube with PMB 3070 can prevent the event that the tube and the tracheal tissue are rubbed against each other to damage the tracheal tissue during the use of the cuffed tracheal tube and at the time of attachment/detachment thereof.

From the fact that inflammation has been induced in a part up to the deep part of the submucosal tissue in FIGS. 7A and 7B, the possibility that a plasticizer has transferred from the cuffed tracheal tube to the tracheal tissue is suggested. On the other hand, no inflammation is observed in the deep part of the submucosal tissue in FIGS. 7C and 7D. Accordingly, it has been demonstrated that the coating of the cuffed tracheal tube with PMB 3070 can prevent the event of transferring the plasticizer from the cuffed tracheal tube to the tracheal tissue.

Example 5

The effect of preventing the elution of the plasticizer obtained by the MPC coating was reviewed in Example 5. Namely, it was considered that, for example, bis(2-ethylhexyl)phthalate (DEHP), as a plasticizer, contained in the tracheal tube may induce cell inflammation. Then, it was studied whether the formation of the coating layer (MPC coating) suppressed the elution of DEHP.

A polyvinyl chloride sheet (PVC sheet) was prepared. In this Example, a copolymer (PMB 3070) including 2-methacryloyloxyethyl phosphorylchlorine (MPC) and n-butyl methacrylate (manufactured by NOF Corporation) was used. PMB 3070 was dissolved with 100% methanol so that the amount thereof reached 0.5% by weight.

A PVC sheet coated with the PMB 3070 solution once [MPC (1×)], a PVC sheet coated with the PMB 3070 solution three times [MPC (3×)] and a PVC sheet having no coating (control experiment: [MPC–]) were prepared. The respective sheets were dipped in 50 ml of ultrapure water, and the temperature was kept at 37° C. The dipping solution was collected at the respective times, 0.5, 1, 2, 4, 6, 8, 12, 24 and 72 hours to measure the absorbance spectrum at 200 nm to 500 nm with an absorptiometer.

FIG. 8 shows a graph alternative to the drawing showing the measurement result of the absorbance spectrum to demonstrate the possibility that the MPC coating may prevent the elution of the plasticizer. FIG. 8(a) shows the absorbance spectrum of the dipping liquid 12 hours after the start of dipping. FIG. 8(b) shows the absorbance spectrum of the dipping liquid 24 hours after the start of dipping. From FIG. 8(a), strong absorption was observed near 270 nm in the PVC sheet not coated with MPC 12 hours after the start of dipping. This means the elution of DEHP. On the other hand, it has been confirmed that the MPC coating suppresses the elution of DEEP. Further, it has been revealed that the MPC lamination enhances the elution effect. From FIG. 8(b), it can be understood that, after 24 hours, the elution of DEHP increases as compared with that after 12 hours. On the other hand, it has been found that the MPC coating suppresses the elution of DEEP also after 24 hours.

Figure 9:
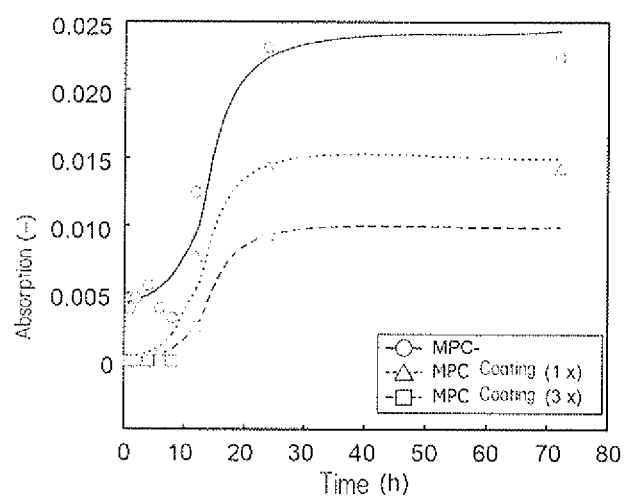
FIG. 9 is a graph that shows the changes in elution time of DEHP when changing the amount of MPC coating.

FIG. 9 shows a graph alternative to the drawing showing the change of the DEEP elution with time when the frequency of MPC coating was changed. The elution of DEEP was observed one hour after the start of dipping in the PVC sheet not coated with MPC, and reached a steady state once near 8 hours after the start of dipping. The DEHP elution tended to increase from about 12 hours after the start of dipping. On the other hand, the MPC coating has clearly been confirmed to suppress the elution of DEHP. Further, the amount of the steady-state DEHP eluted was reduced in the order of MPC–

(control), MPC (1×) and MPC (3×). It has been demonstrated, from this fact, that the lamination of the MPC coating can suppress the elution of DEHP more. This result suggests the possibility that the DEEP eluted from the PVC sheets may have been trapped by MPC.

Example 6

The effect, by the MPC coating, of suppressing inflammatory reactions caused by the elution of the plasticizer was studied in Example 6. A PVC sheet free of DEHP (DEHP−), a PVC sheet not coated with MPC (MPC−), a PVC sheet coated with MPC once [MPC (1×)] and a PVC sheet coated with MPC three times [MPC (3×)] were prepared. The respective sheets were dipped in a DMEM medium containing 10% FBS, and left at 37° C. for 8 hours. During the period, the medium was collected after 0, 1, 2, 4 and 8 hours. As a control experiment, a normal medium containing no PVC sheet (−) was also kept in temperature at 37° C., and collected at similar times. The PVC-dipping medium was added to RAW 264.7 cells being cultured in a 6-well plate, and, after 8-hour cultivation, TNF-α and prostaglandin E$_2$ (PGE2) in the medium were measured by the ELISA method. FIG. 10 shows the results.

FIG. 10 shows a graph alternative to the drawing showing the effect, by the MPC coating, of suppressing the inflammatory reactions derived from the DEHP released from PVC. FIG. 10(a) shows the measurement result of TNF-α in the medium. FIG. 10(b) shows the measurement result of prostaglandin E$_2$ (PGE2) in the medium. From FIG. 10, no rise in TNF-α or PGE2 has been confirmed when using the medium in which the PVC sheet containing no DEHP (DEHP−) was dipped. On the other hand, when using the medium in which the normal PVC sheet including DEHP was dipped, the increase in production of TNF-α and PGE2 with time was recognized. Thus, it has been revealed that DEEP is eluted from the PVC sheet, thereby inducing inflammatory reactions.

FIG. 11 shows a graph alternative to the drawing showing inflammatory reactions derived from the DEHP released from PVC using a medium in which a PVC sheet was dipped for 8 hours. FIG. 11(a) shows the measurement result of TNF-α in the medium. FIG. 11(b) shows the measurement result of prostaglandin E$_2$ (PGE2) in the medium. Through the experiment, it was recognized that the DEHP eluted from the PVC sheet increases the production of TNF-α and PGE2 and induces inflammatory reactions. Further, it was found that the inflammatory reactions generated by DEHP are clearly suppressed by carrying out MPC coating. From this result, it has been revealed that the MPC coating can suppress the elution, from PVC, of DEHP which can be harmful to living organisms. It has also been found that the effect of suppressing the elution of DEHP is enhanced by laminating the MPC coating layer.

Study on the effect of preventing damage on tracheal mucosa obtained by MPC-coated tube.

Example 7

In Example 7, it was reviewed whether the tissue damage on the tracheal mucosa caused by a PVC tube is suppressed by carrying out MPC coating.

From a canine into which a PVC breathing assistance tube subjected to MPC coating and a PVC breathing assistance tube not subjected to MPC coating [MPC coating (1×) and MPC−] were each inserted, the site in contact with the cuff part and its peripheral tracheal wall were collected. The collected tissues were fixed with 10% formalin, and, thereafter, paraffin-embedded sections were prepared. The sections were subjected to hematoxylin-eosin staining (HE staining) or PAS staining used as general staining for carbohydrate to histologically analyze the sections.

Figure 12:
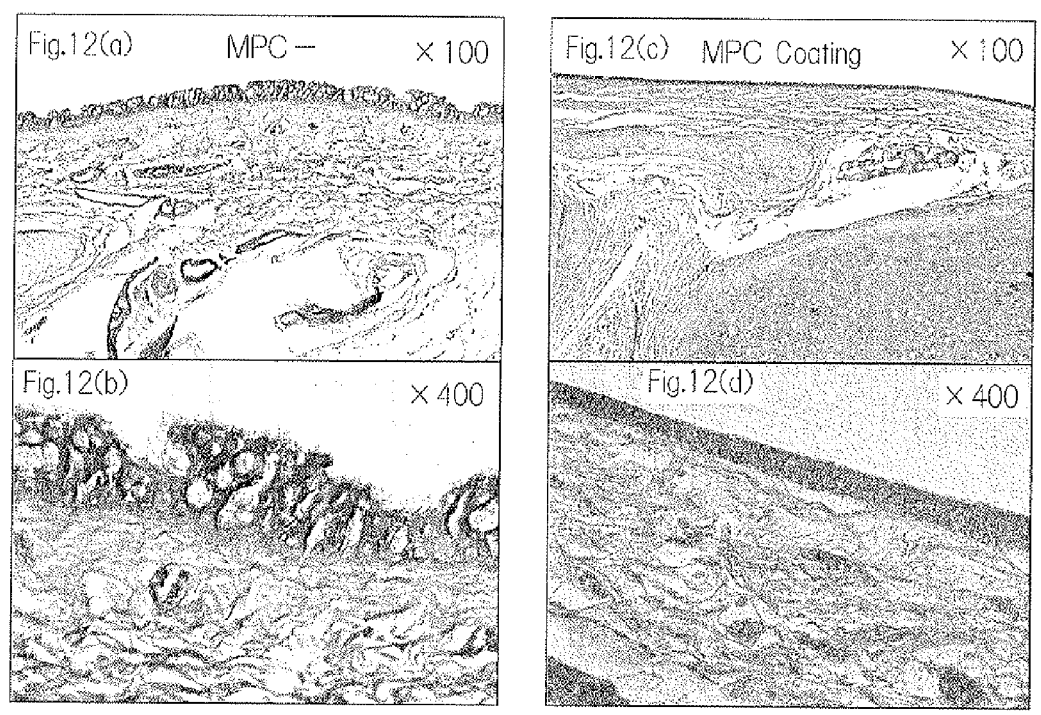
FIG. 12 are photographs that show the results of dyeing in HE.

FIG. 12 shows a photograph alternative to the drawing indicating the results of HE staining. FIG. 12(a) shows the result of HE staining with respect to the PVC breathing assistance tube not subjected to MPC coating (MPC−). FIG. 12(b) is an enlarged view of FIG. 12(a). FIG. 12(c) shows the result of HE staining with respect to the PVC breathing assistance tube subjected to MPC coating (MPC coating (1×)). FIG. 12(d) is an enlarged view of FIG. 12(c). From FIG. 12, it has been revealed that the tracheal mucosal tissue is significantly damaged upon contact with the cuff part. Further, it has been revealed that tissue damage is suppressed by carrying out MPC coating.

Figure 13:
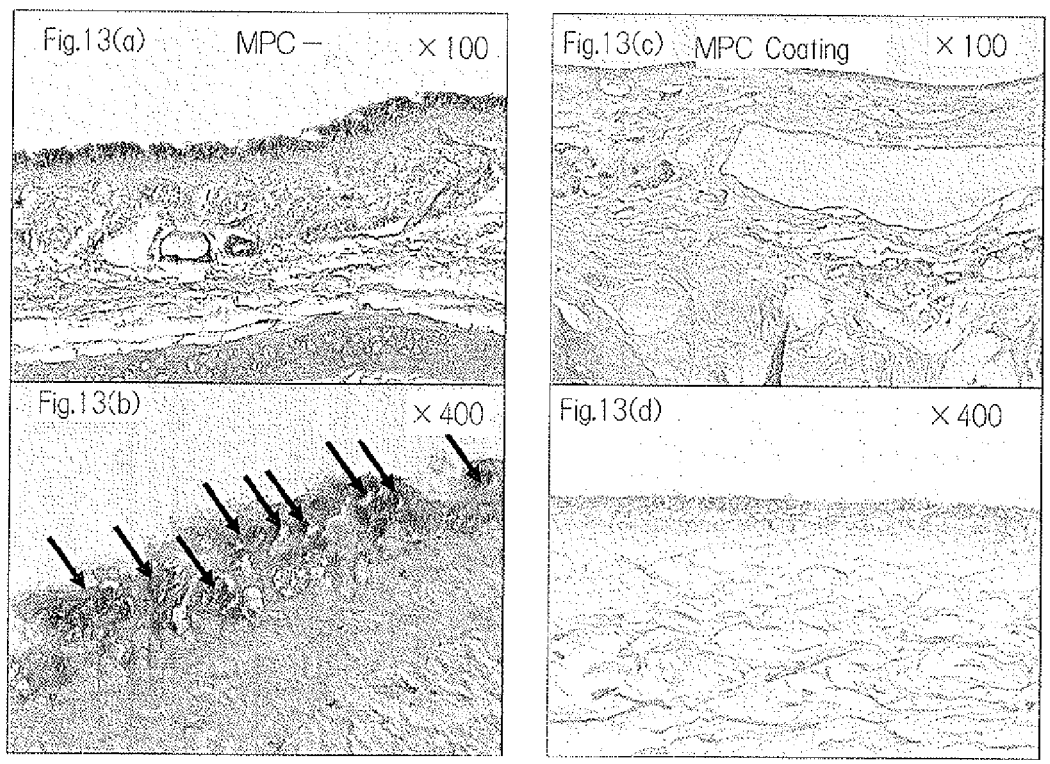
FIG. 13 are photographs that show the results of dyeing in PAS.

FIG. 13 shows a photograph alternative to the drawing showing the results of PAS staining. FIG. 13(a) shows the result of PAS staining with respect to the PVC breathing assistance tube not subjected to MPC coating (MPC−). FIG. 13(b) is an enlarged view of FIG. 13(a). FIG. 13(c) shows the result of PAS staining with respect to the PVC breathing assistance tube subjected to MPC coating (MPC coating (1×)). FIG. 13(d) is an enlarged view of FIG. 13(c). From FIG. 13, it has been revealed that the production of goblet cells (arrow) responsible for mucus secretion increases in association with the damage on the tracheal mucosa. Further, it has been revealed that the increase in production of goblet cells tends to be suppressed by carrying out MPC coating.

FIG. 14 shows a photograph alternative to the drawing showing the results of HE staining and PAS staining in peripheral tissues in which the exfoliation of the epithelium of the tracheal mucosa was observed. FIG. 14(a) shows the result of HE staining with respect to the PVC breathing assistance tube not subjected to MPC coating (MPC−). FIG. 14(b) shows the result of PAS staining with respect to the PVC breathing assistance tube not subjected to MPC coating (MPC−). From FIG. 14, a remarkable increase in goblet cells has been recognized also in peripheral tissues in which the exfoliation of the epithelium of the tracheal mucosa was observed.

INDUSTRIAL APPLICABILITY

The present invention can be widely utilized in the medical instrument industry.

The invention claimed is:

1. A respiratory support tube having a coating layer on the surface thereof,
   wherein the coating layer of the respiratory support tube has polymer that comprises 2-methacryloyloxy ethyl phosphorylcholine.

2. A respiratory support tube having a coating layer on the surface,
   wherein the coating layer of the respiratory support tube has co-polymer of 2-methacryloyloxy ethyl phosphorylcholine and hydrophobic monomer, the co-polymer is represented by formula (I):

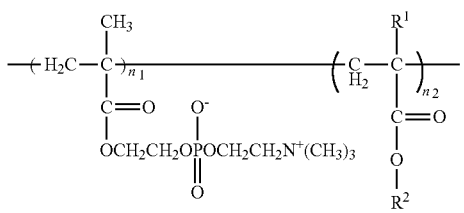

in the formula (I), $n_1$ and $n_2$ represent an integer from 20 to 1500 that may be the same or different;

$R^1$ represents H, or $C_{1-3}$ alkyl group; and $R^2$ represents $C_{4-15}$ alkyl group, $C_{4-15}$ alkenyl group, or $C_{4-15}$ alkynyl group.

3. A respiratory support tube having a coating layer on the surface, wherein the coating layer of the respiratory support tube has co-polymer of 2-methacryloyloxy ethyl phosphorylcholine and basic monomer, the co-polymer is represented by formula (II):

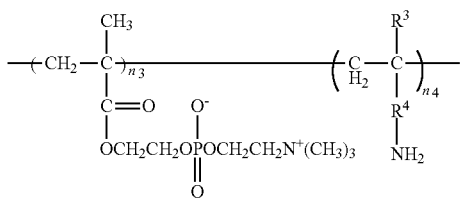

in the formula (II), $n_3$ and $n_4$ represent an integer from 20 to 1500 that may be the same or different;

$R^3$ represents H, or $C_{1-3}$ alkyl group;

$R^4$ represents $C_{1-8}$ alkylene group, $C_{2-7}$ alkenylene group, or $C_{2-7}$ alkynylene group, or a group that is represented as (—COO—$R^5$—); and $R^5$ represents $C_{1-8}$ alkylene group, $C_{2-7}$ alkenylene group, or $C_{2-7}$ alkynylene group.

4. The respiratory support tube in accordance with any one of claims 1-3, wherein the thickness of the coating layer is from $1 \times 10^0$ to $1 \times 10^4$ μm.

5. The respiratory support tube in accordance with any one of claims 1-3, wherein the coating layer further comprises trehalose.

6. The respiratory support tube in accordance with any one of claims 1-3, wherein the respiratory support tube is:

an endotracheal tube, a bronchial tube, a tracheostomy tube, a laryngeal tracheal tube, or an esophagus tube.

7. The respiratory support tube in accordance with claim 6, wherein the tube has a cuff attached to the tube.

8. A method for coating the respiratory support tube, wherein the method comprise a process of coating the respiratory support tube with a coating solution having 0.01 to 50 wt % polymer comprising 2-methacryloyloxy ethyl phosphorylcholine.

9. The method in accordance with claim 8, wherein the coating process comprise immersing the respiratory support tube in the coating solution, drying the coated respiratory support tube, repeating the immersion and the drying process 2 to 20 times.

* * * * *